US012584923B2

(12) United States Patent　　　　　　(10) Patent No.: US 12,584,923 B2
Hill et al.　　　　　　　　　　　　　　　(45) Date of Patent: Mar. 24, 2026

(54) APPARATUS AND METHODS FOR FABRICATION OF NANOPATTERNED ARRAYS

(71) Applicants: UNIVERSITY OF WYOMING, Laramie, WY (US); University of New Hampshire, Durham, NH (US)

(72) Inventors: Caleb Hill, Laramie, WY (US); Jeffrey Halpern, Durham, NH (US)

(73) Assignee: UNIVERSITY OF WYOMING, Laramie, WY (US)

( * ) Notice: Subject to any disclaimer, the term of this patent is extended or adjusted under 35 U.S.C. 154(b) by 901 days.

(21) Appl. No.: 17/584,167

(22) Filed: Jan. 25, 2022

(65) Prior Publication Data

US 2022/0326254 A1　　Oct. 13, 2022

Related U.S. Application Data

(60) Provisional application No. 63/141,433, filed on Jan. 25, 2021.

(51) Int. Cl.
　B82B 3/00　　　(2006.01)
　B82Y 40/00　　　(2011.01)
　G01N 33/543　　　(2006.01)
　G01N 33/68　　　(2006.01)
　(Continued)

(52) U.S. Cl.
　CPC ....... G01N 33/6869 (2013.01); B82B 3/0014 (2013.01); G01N 33/54346 (2013.01); G01N 33/54373 (2013.01); G01N 33/74 (2013.01); B82Y 5/00 (2013.01); B82Y 40/00 (2013.01)

(58) Field of Classification Search
　CPC ...... C25D 1/006; C25D 5/02; G01N 33/6869; G01N 33/54346; G01N 33/54373; G01N 33/74
　See application file for complete search history.

(56) References Cited

U.S. PATENT DOCUMENTS

| | | | |
|---|---|---|---|
| 6,524,462 B1 * | 2/2003 | Lowe | C25D 5/06 205/125 |
| 7,955,486 B2 * | 6/2011 | Yu | C25D 17/00 205/133 |

(Continued)

OTHER PUBLICATIONS

Saha et al., "Probing Electrocatalysis at Individual Au Nanorods via Correlated Optical and Electrochemical Measurements", Anal. Chem., vol. 90, pp. 12832-12839, Oct. 2018.

(Continued)

*Primary Examiner* — Michael P Wieczorek
(74) *Attorney, Agent, or Firm* — Patterson + Sheridan, LLP

(57) ABSTRACT

A method of fabricating an array on nanoparticles includes forming a solution containing a material precursor and an electrolyte. The solution is laded into a pipet and a wire is inserted into the solution. The pipet is brought into contact with a substrate and an electrical bias is applied between the substrate and the wire. A nanoparticle is formed via electrodeposition. The steps of bring a pipet into contact with the substrate, applying an electrical bias, and forming a nanoparticle across an array of contact points to create the array of nanoparticles. The substrate is rinsed with a solvent to remove residual electrolytes.

25 Claims, 18 Drawing Sheets
(4 of 18 Drawing Sheet(s) Filed in Color)

(51) Int. Cl.
  *G01N 33/74*          (2006.01)
  *B82Y 5/00*           (2011.01)

(56) References Cited

U.S. PATENT DOCUMENTS

| 9,316,613 B2* | 4/2016 | Unwin | G01Q 60/60 |
| 12,202,193 B2* | 1/2025 | Eliyahu | B22F 10/10 |

OTHER PUBLICATIONS

Saha et al., "Supporting Information—Probing Electrocatalysis at Individual Au Nanorods via Correlated Optical and Electrochemical Measurements", University of Wyoming, 2018.

Nikoobahkht et al., "Preparation and Growth Mechanism of Gold Nanorods (NRs) Using Seed-Mediated Growth Method", Chem. Mater. 2003, vol. 15, Issue 10, pp. 1957-1962, Apr. 2003.

Xiao et al., "Current Transients in Single Nanoparticle Collision Events", J. Am. Chem. Soc., vol. 130, Issue 49, pp. 16669-16677, Jul. 2008.

Lide, "CRC Handbook of Chemistry and Physics", 89th Edition, CRC Press, 2008.

Eisner et al., "Anodic oxidation of hydrazine and its derivatives: Part I. The oxidation of hydrazine on gold electrodes in acid solutions", J. Electroanal. Chem. Interfacial Electrochem., vol. 28, Issue 1, pp. 81-92, Nov. 1970.

Chen et al., "Voltammetric Scanning Electrochemical Cell Microscopy: Dynamic Imaging of Hydrazine Electro-oxidation on Platinum Electrodes", Anal. Chem., vol. 87, Issue 11, pp. 5782-5789, May 2015.

Rosca et al., "Electrocatalytic oxidation of hydrazine on platinum electrodes in alkaline solutions", Electrochim. Acta, vol. 53, Issue 16, pp. 5199-5205, Jun. 2008.

Anderson et al., "Single-Nanoparticle Electrochemistry through Immobilization and Collision", Acc. Chem. Res., vol. 49, Issue 11, pp. 2625-2631, Oct. 2016.

Kleijn et al., "Landing and Catalytic Characterization of Individual Nanoparticles on Electrode Surfaces", J. Am. Chem. Soc., vol. 134, Issue 45, pp. 18558-18561, Oct. 2012.

Li et al., "Electrochemical Responses and Electrocatalysis at Single Au Nanoparticles", J. Am. Chem. Soc., vol. 132, Issue 9, pp. 3047-3054, Feb. 2010.

Chen et al., "Electrodeposition of Platinum on Nanometer-Sized Carbon Electrodes", J. Phys. Chem. B, vol. 107, Issue 33, pp. 8392-8402, Jul. 2003.

Chen et al., "Electrocatalysis under Conditions of High Mass Transport Rate: Oxygen Reduction on Single Submicrometer-Sized Pt Particles Supported on Carbon", J. Phys. Chem. B, vol. 108, Issue 10, pp. 3262-3276, Feb. 2004.

Chen et al., "Electrocatalysis under Conditions of High Mass Transport: Investigation of Hydrogen Oxidation on Single Submicron Pt Particles Supported on Carbon", J. Phys. Chem. B, vol. 108, Issue 37, pp. 13984-13994, Aug. 2004.

Zhou et al., "Electrodeposition of Isolated Platinum Atoms and Clusters on Bismuth-Characterization and Electrocatalysis", J. Am. Chem. Soc., vol. 139, Issue 48, pp. 17677-17682, Nov. 2017.

Dick et al., "Recognizing Single Collisions of PtCl62—at Femtomolar Concentrations on Ultramicroelectrodes by Nucleating Electrocatalytic Clusters", J. Am. Chem. Soc., vol. 137, Issue 43, pp. 13752-13755, Oct. 2015.

Fernando et al., "Observation of Individual Semiconducting Nanoparticle Collisions by Stochastic Photoelectrochemical Currents", J. Am. Chem. Soc., vol. 135, Issue 30, pp. 10894-10897, Jul. 2013.

Percival et al., "Fast-Scan Cyclic Voltammetry Allows Determination of Electron-Transfer Kinetic Constants in Single Nanoparticle Collision", J. Phys. Chem. C, vol. 120, Issue 37, pp. 20536-20546, Mar. 2016.

Jiao et al., "Hydrogen Oxidation Reaction on Platinum Nanoparticles: Understanding the Kinetics of Electrocatalytic Reactions via "Nano-Impacts"", J. Phys. Chem. C, vol. 120, Issue 24, pp. 13148-13158, Jun. 2016.

Hao et al., "Imaging Dynamic Collision and Oxidation of Single Silver Nanoparticles at the Electrode/Solution Interface", J. Am. Chem. Soc., vol. 139, Issue 35, pp. 12274-12282, Aug. 2017.

Quinn et al., "Time-Resolved Electrochemical Detection of Discrete Adsorption Events", J. Am. Chem. Soc., vol. 126, Issue 27, pp. 8360-8361, Jun. 2004.

Zhou et al., "Observation of Discrete Au Nanoparticle Collisions by Electrocatalytic Amplification Using Pt Ultramicroelectrode Surface Modification", J. Phys. Chem. Lett., vol. 1, Issue 18, pp. 2671-2674, Aug. 2010.

Xiao et al., "Observing Single Nanoparticle Collisions at an Ultramicroelectrode by Electrocatalytic Amplification", J. Am. Chem. Soc., vol. 129, Issue 31, pp. 9610-9612, Jul. 2007.

Brasiliense et al., "Correlated Electrochemical and Optical Detection Reveals the Chemical Reactivity of Individual Silver Nanoparticles", J. Am. Chem. Soc., vol. 138, Issue 10, pp. 3478-3483, Feb. 2016.

Kim et al., "Electrocatalytic Activity of Individual Pt Nanoparticles Studied by Nanoscale Scanning Electrochemical Microscopy", J. Am. Chem. Soc., vol. 138, Issue 27, pp. 8560-8568, Jun. 2016.

Kim et al., "Nanometer Scale Scanning Electrochemical Microscopy Instrumentation", Anal. Chem., vol. 88, Issue 20, pp. 10284-10289, Sep. 2016.

Yu et al., "Scanning Electrochemical Microscopy of Single Spherical Nanoparticles: Theory and Particle Size Evaluation", Anal. Chem., vol. 87, Issue 14, pp. 7446-7453, Jul. 2015.

Sun et al., "Scanning Electrochemical Microscopy of Individual Catalytic Nanoparticles", Angew. Chem., Int. Ed., vol. 53, Issue 51, pp. 14120-14123, Oct. 2014.

Blanchard et al., "Scanning Electrochemical Microscopy Study of Permeability of a Thiolated Aryl Multilayer and Imaging of Single Nanocubes Anchored to It", Langmuir, vol. 32, Issue 10, pp. 2500-2508, Feb. 2016.

Bentley et al., "Nanoscale Structure Dynamics within Electrocatalytic Materials", J. Am. Chem. Soc., vol. 139, Issue 46, pp. 16813-16821, Oct. 2017.

Kang et al., "Simultaneous Topography and Reaction Flux Mapping at and around Electrocatalytic Nanoparticles", ACS Nano, vol. 11, Issue 9, pp. 9525-9535, Sep. 2017.

Snowden et al., "Scanning Electrochemical Cell Microscopy: Theory and Experiment for Quantitative High Resolution Spatially-Resolved Voltammetry and Simultaneous Ion-Conductance Measurements", Anal. Chem., vol. 84, Issue 5, pp. 2483-2491, Jan. 2012.

Güell et al., "Mapping Nanoscale Electrochemistry of Individual Single-Walled Carbon Nanotubes", Nano Lett., vol. 14, Issue 1, pp. 220-224, Nov. 2013.

Ebejer et al., "Scanning Electrochemical Cell Microscopy: A Versatile Technique for Nanoscale Electrochemistry and Functional Imaging", vol. 6, Issue 1, pp. 329-351, Jun. 2013.

Aaronson et al., "Pseudo-Single-Crystal Electrochemistry on Polycrystalline Electrodes: Visualizing Activity at Grains and Grain Boundaries on Platinum for the Fe2+/Fe3+ Redox Reaction", J. Am. Chem. Soc., vol. 135, Issue 10, pp. 3873-3880, Feb. 2013.

Wang et al., "Plasmonic Imaging of Surface Electrochemical Reactions of Single Gold Nanowires", J. Am. Chem. Soc., vol. 139, Issue 4, pp. 1376-1379, Jan. 2017.

Brasiliense et al., "Opto-electrochemical In Situ Monitoring of the Cathodic Formation of Single Cobalt Nanoparticles", Angew. Chem., Int. Ed., vol. 56, Issue 35, pp. 10598-10601, Jun. 2017.

Brasiliense et al., "Electrochemical transformation of individual nanoparticles revealed by coupling microscopy and spectroscopy," Faraday Discuss., vol. 193, pp. 339-352, May 2016.

Hoener et al., "Spectral Response of Plasmonic Gold Nanoparticles to Capacitive Charging: Morphology Effects", J. Phys. Chem. Lett., vol. 8, Issue 12, pp. 2681-2688, May 2017.

Chirea et al., "Spectroelectrochemistry of Silver Deposition on Single Gold Nanocrystals", J. Phys. Chem. Lett., vol. 5, Issue 24, pp. 4331-4335, Nov. 2014.

(56)        References Cited

OTHER PUBLICATIONS

Shan et al., "Imaging the electrocatalytic activity of single nanoparticles", Nat. Nanotechnol., vol. 7, Issue 10, pp. 668-672, Aug. 2012.

Wang et al., "Detection, Counting, and Imaging of Single Nanoparticles", Anal. Chem., vol. 86, Issue 1, pp. 2-14, Dec. 2013.

Fang et al., "Plasmonic Imaging of Electrochemical Oxidation of Single Nanoparticles", J. Am. Chem. Soc., vol. 136, Issue 36, pp. 12584-12587, Aug. 2014.

Shan et al., "Imaging Local Electrochemical Current via Surface Plasmon Resonance", Science, vol. 327, Issue 5971, pp. 1363-1366, Mar. 2010.

Hill et al., "A Dark-Field Scattering Spectroelectrochemical Technique for Tracking the Electrodeposition of Single Silver Nanoparticles", J. Am. Chem. Soc., vol. 135, Issue 46, pp. 17250-17253, Oct. 2013.

Hill et al., "Single Ag Nanoparticle Spectroelectrochemistry via Dark-Field Scattering and Fluorescence Microscopies", vol. 119, Issue 12, pp. 6760-6768, Mar. 2015.

Pan et al., "Observation of Local Redox Events at Individual Au Nanoparticles Using Electrogenerated Chemiluminescence Microscopy", J. Phys. Chem. C, vol. 119, Issue 48, pp. 27095-27103, Nov. 2015.

Hill et al., "Combined optical and electrochemical methods for studying electrochemistry at the single molecule and single particle level: recent progress and perspectives", Phys. Chem. Chem. Phys., vol. 15, Issue 48, pp. 20797-20807, Oct. 2013.

Novo et al., "Electrochemical Charging of Single Gold Nanorods", J. Am. Chem. Soc., vol. 131, Issue 41, pp. 14664-14666, Sep. 2009.

Collins et al., "Single Gold Nanorod Charge Modulation in an Ion Gel Device", Nano Lett. vol. 16, Issue 11, pp. 6863-6869, Oct. 2016.

Novo et al., "Direct observation of chemical reactions on single gold nanocrystals using surface plasmon spectroscopy", vol. 3, Issue 10, pp. 598-602, Sep. 2008.

Zou et al., "Cooperative communication within and between single nanocatalysts", Nat. Chem., vol. 10, Issue 6, pp. 607-614, Mar. 2018.

Sambur et al., "Sub-particle reaction and photocurrent mapping to optimize catalyst-modified photoanodes", Nature, vol. 530, Issue 7588, pp. 77-80, Feb. 2016.

Sambur et al., "Distinguishing Direct and Indirect Photoelectrocatalytic Oxidation Mechanisms Using Quantitative Single-Molecule Reaction Imaging and Photocurrent Measurements", J. Phys. Chem. C, vol. 120, Issue 37, pp. 20668-20676, May 2016.

Chen et al., "Single-Molecule Nanocatalysis Reveals Catalytic Activation Energy of Single Nanocatalysts", J. Am. Chem. Soc., vol. 138, Issue 38, pp. 12414-12421, Aug. 2016.

Sambur et al., "Approaches to Single-Nanoparticle Catalysis", Annu. Rev. Phys. Chem., vol. 65, Issue 1, pp. 395-422, Jan. 2014.

Shen et al., "Single-molecule nanoscale electrocatalysis", Phys. Chem. Chem. Phys., vol. 12, Issue 25, pp. 6555-6563, Apr. 2010.

Zhou et al., "Size-Dependent Catalytic Activity and Dynamics of Gold Nanoparticles at the Single-Molecule Level", J. Am. Chem. Soc., vol. 132, Issue 1, pp. 138-146, Dec. 2009.

Chen et al., "Single-molecule fluorescence imaging of nanocatalytic processes", Chem. Soc. Rev., vol. 39, Issue 12, pp. 4560-4570, Oct. 2010.

Zaleski et al., "Investigating Nanoscale Electrochemistry with Surface- and Tip-Enhanced Raman Spectroscopy", Acc. Chem. Res., vol. 49, Issue 9, pp. 2023-2030, Sep. 2016.

Johnson et al., "Optical Constants of the Noble Metals", Phys. Rev. B, vol. 6, Issue 12, pp. 4370-4379, Dec. 1972.

Oesch et al., "Electrochemical study of gold electrodes with anodic oxide films—I. Formation and reduction behaviour of anodic oxides on gold", Electrochim. Acta, vol. 28, Issue 9, pp. 1237-1246, Sep. 1983.

Byers et al., "Single-Particle Spectroscopy Reveals Heterogeneity in Electrochemical Tuning of the Localized Surface Plasmon", J. Phys. Chem. B, vol. 118, Issue 49, pp. 14047-14055, Jun. 2014.

Link et al., "Simulation of the Optical Absorption Spectra of Gold Nanorods as a Function of Their Aspect Ratio and the Effect of the Medium Dielectric Constant", J. Phys. Chem. B, vol. 103, Issue 16, pp. 3073-3077, Apr. 1999.

Lee et al., "Dependence of the Enhanced Optical Scattering Efficiency Relative to That of Absorption for Gold Metal Nanorods on Aspect Ratio, Size, End-Cap Shape, and Medium Refractive Index", J. Phys. Chem. B, vol. 109, Issue 43, pp. 20331-20338, Oct. 2005.

* cited by examiner

102

102

EXTENDED STATE
BEFORE ANALYTE BINDING

INTERMEDIATE STATE
SOME ANALYTE BINDING

COLLAPSED STATE
SATURATED SURFACE $k_d = 10^{-10}$ M; $10^{-9}$ M; $10^{-7}$ M;

ELP STIMULI-RESPONSIVE BEHAVIOR

"off"
(e.g. 4 °C
below $T_t$)

270

"on"
(e.g. 37 °C
above $T_t$)

"COLLAPSE"

REPRESENTATIVE ELP STRUCTURE $[VPGIG]_n$

FIG. 12

APPARATUS AND METHODS FOR FABRICATION OF NANOPATTERNED ARRAYS

CROSS-REFERENCE TO RELATED APPLICATIONS

This application claims benefit of U.S. Provisional Patent Application No. 63/141,433, filed Jan. 25, 2021, the entirety of which is herein incorporated by reference.

BACKGROUND

Field

Embodiments of the present disclosure generally relate to methods for fabrication of nanopatterned arrays and selective functionalization of nanoparticles ("NPs") of an ordered array.

Description of the Related Art

The controlled placement of nanoscale entities on substrates has been explored previously via methods such as self-assembly onto lithographically patterned substrates, dip-pen lithography, or optical trapping. However, these methods carry significant limitations in terms of throughput or applicability to electrochemical systems.

Many nanoparticle-based sensing technologies employ drop-coated arrays of structures, where the random orientation introduces significant reproducibility issues due to the variations in optical properties, accessibility of analytes to particle surfaces, and other considerations.

It is contemplated that spatial control over the morphology and surface chemistry of heterogeneous interfaces is required to achieve reliable, multiplexed electrochemical sensing. Existing methods for the fabrication of these interfaces cannot achieve a sufficiently high degree of control, significantly limiting the development of effective sensing platforms.

Transduction methods of in-line electrochemical protein biosensors typically tag the surface motif with an active electrochemical signal to monitor analyte response with voltammetry or amperometry. The ability to electrochemically monitor binding events without an active electrochemical tag would expand the diversity of analytes and ease of measurement for point-of-need process analytical capabilities in the advance biomanufacturing industry.

Proteins with compelling functions are not efficiently translated into industrially viable sensors utilizing conventional methodologies because aspects of the sensor fabrication process, such as labeling proteins with probes or immobilizing proteins on a surface, are often incompatible with stable protein function. Proteins designed to perform within the context of a given application or have functionality independent of a given context would dramatically simplify the development of protein-based sensors.

SUMMARY

In one embodiment, a method of fabricating an array of nanoparticles is disclosed. The method includes pre-synthesizing a plurality of nanoparticle, forming a solution of nanoparticles and solvent, and loading the solution into a pipet and bringing the pipet into contact with a substrate at an array of contact points. The method also includes depositing an array of solution droplets at the corresponding array of contact points, wherein each of the solution droplets contains a nanoparticle, and evaporating the solvent from the solution droplet to form the array of nanoparticles.

In another embodiment, a method of fabricating an array of nanoparticles is disclosed. The method includes forming a solution containing a material precursor and an electrolyte and loading the solution into a pipet. The method further includes inserting a wire into the solution, bringing a pipet into brief contact with a substrate, and applying an electrical bias between the substrate and the wire, resulting in the forming of a nanoparticle via electrodeposition. The method also includes repeating the bringing the pipet into brief contact with the substrate, applying an electrical bias between the substrate and the wire, and forming a nanoparticle via electrodeposition across an array of contact points to create nanoparticle array. The method also includes rinsing the substrate with a solvent to remove residual electrolytes.

In yet another embodiment, a method of fabricating an array of nanoparticles is disclosed. The method includes forming a solution containing a material precursor and a reactive species and loading the solution into a pipet, depositing an array of droplets of the solution across an array of contact points, and initiating a chemical reaction between the material precursor and the reactive species in the array of droplets to form a nanoparticle as a result of the chemical reaction. The method also includes rinsing the substrate with solvent to remove residual reactants.

In yet another embodiment, a biosensor for monitoring surface binding events is disclosed. The biosensor includes an array of nanoparticles and an analyte responsive polymer. The array of nanoparticles includes a plurality of nanoparticles distributed across an array of contact points and the analyte responsive polymer includes a recognition element at a first end of the polymer and a terminus at a second end of the polymer distal from the recognition element. The terminus is conjugated to the nanoparticles in the nanoparticle array. When the recognition element reacts with an analyte, the analyte responsive polymer creates a change in the electrochemical signal at the surface of the nanoparticle array that can be measured to monitor surface events of the analyte responsive polymer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 12 illustrates an elastin-like polymer undergoing a triggered and reversible extension and collapse according to an embodiment of the disclosure.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The descriptions of various aspects of the present disclosure have been presented for purposes of illustration, but are not intended to be exhaustive or limited to the aspects disclosed. Many modification and variations will be apparent to those of ordinary skill in the art without departing from the scope and spirit of the described aspects. The terminology used herein was chosen to best explain the principles of the aspects, the practical application or technical improvement over technologies found in the marketplace, or to enable one of ordinary skill in the art to understand the aspects disclosed herein.

Many nanoparticle-based sensing technologies employ drop-coated arrays of structures, where the random orientation introduces significant reproducibility issues due to the variations in optical properties, accessibility of analytes to particle surfaces, and other considerations. Due to the propensity of drop-coated arrays to exhibit significant reproducibility issues, it is desirable to develop methods to generate arrays which exhibit improved reproducibility. The methods described herein provide the ability to efficiently fabricate controlled arrays of nanostructures and to form arrays with controlled distributions at submicron length scales. The methods described herein generate arrays which do not suffer from these drawbacks and improve the reproducibility and detection limits of a variety of arrays. Embodiments of the present disclosure have application in optical or electrochemical sensors, but may be utilized in a variety of other applications.

Figure 1:
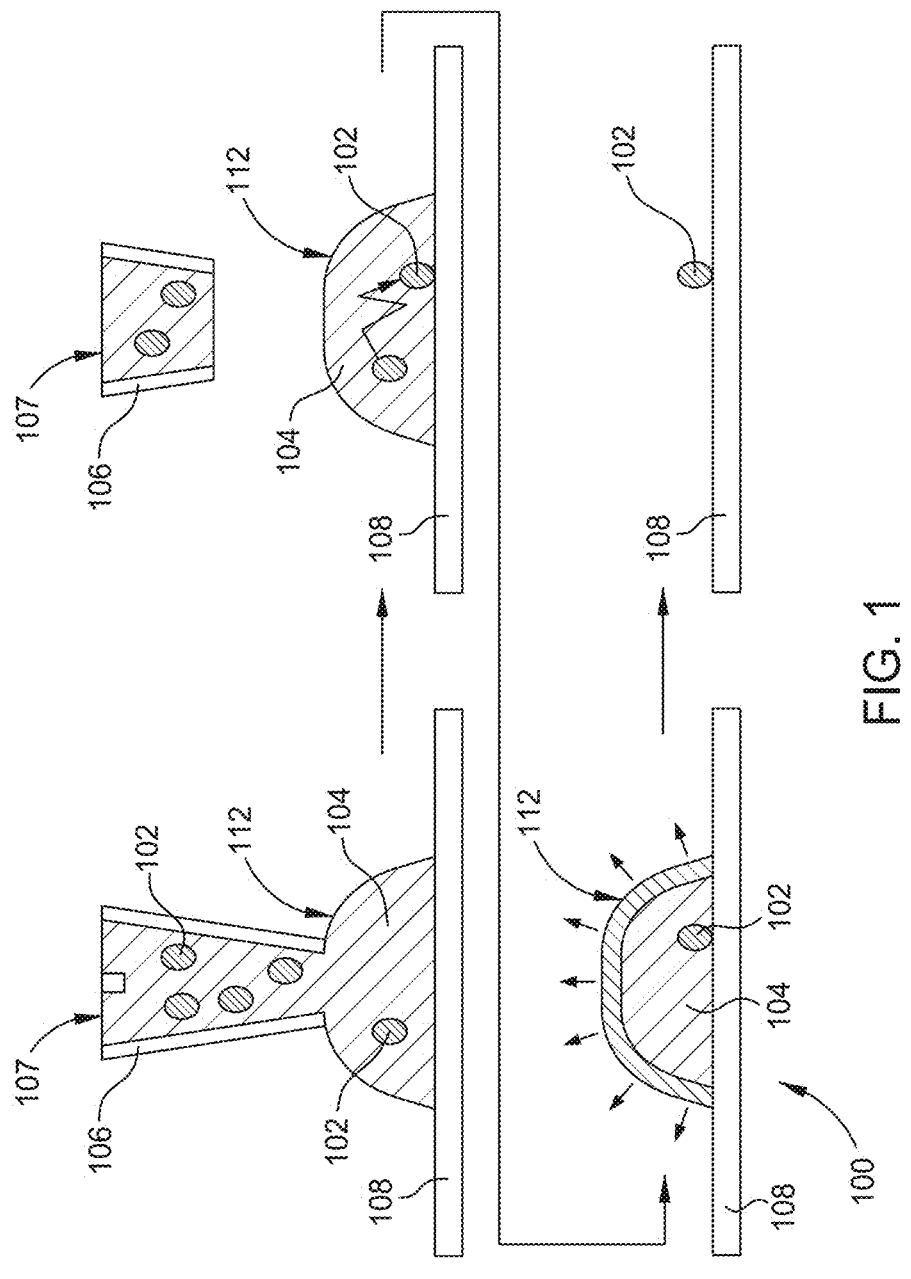
FIG. 1 illustrates a schematic of a method of fabricating a nanoparticle array using a pipet-based method according to an embodiment of the disclosure.

Referring to FIG. 1, a pipet-based approach to creating a nanoparticle array is shown, generally referred to as reference numeral 100. The method includes pre-synthesizing a plurality of nanoparticles 102 and forming a solution 107 of the nanoparticles with a solvent 104. Once the solution 107 of solvent 104 and nanoparticles 102 has been formed, the method includes loading the solution into a pipet 106. The pipet 106 is configured to have a submicron tip dimension in order to control distribution at submicron length scales. Next, the method includes bringing the pipet 106 into contact with a substrate 108 at an array of contact points 110 and depositing an array of solution droplets 112 at the corresponding contact points, each of the droplets containing an individual nanoparticle 102. The array of contact points 110 are preprogrammed into a positioning system, described below. Finally, the method includes evaporating the solvent 104 from the solution droplets 112 to form the array of nanoparticles 102.

Figure 2:
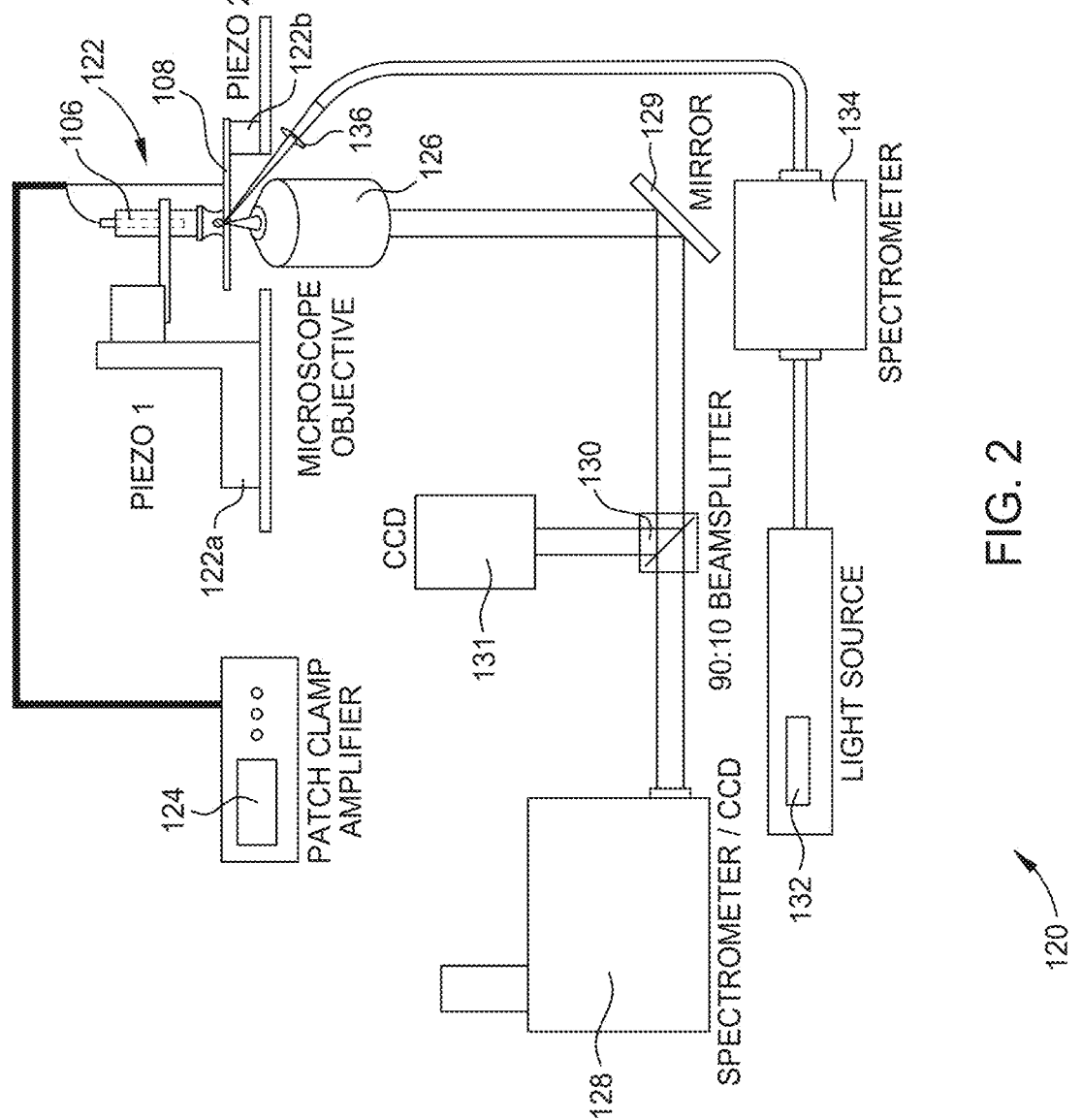
FIG. 2 illustrates a TECCM apparatus according to an embodiment of the disclosure.

Referring to FIG. 2, a Targeted ElectroChemical Cell Microscopy (TECCM) apparatus 120 is shown. In one embodiment of the pipet-based approach 100, the TECCM apparatus 120 is enabled. The TECCM apparatus 120 includes positioning system 122 (i.e., a Piezo positioning system), an amplifier 124, a microscopic objective 126, a first spectrometer 128, a mirror 129, a beamsplitter 130, a charge coupled device 131, a light source 132, a second spectrometer 134, and a lens 136. The TECCM apparatus 120 is based on correlated optical and electroanalytical measurements and is used to fabricate ordered arrays of nanoparticles 102. The positioning system 122 further includes a first piezo 122*a* and a second piezo 122*b*. The pipet positing system 122 controls the x, y, and z, position of the pipet 106 with respect to the substrate 108. The first and second piezos 122*a*, 122*b* are used to locally address the pipet 106 to the substrate 108 with the solution containing the nanoparticles 102. The first piezo 122*a* brings the pipet 106 into contact with the substrate 108 and detects the contact through a pressure induced electrical output of the first and second piezo.

Once the measurement has reached the desired threshold, the first and second piezo 122*a*, 122*b* release the contact between the pipet 106 and the substrate 108, leaving a solution droplet 112. By monitoring the measurements of the first and second piezo 122*a*, 122*b*, the concentration of the solution being deposited can be controlled, leaving a single nanoparticle 102 trapped within the droplet 112. The nanoparticle 102 then attaches to the substrate 108 through absorption or covalent attachment. The TECCM apparatus 120 utilizes the microscopic objective 126 and the lens 136 to monitor the progress of the nanoparticle array 101 construction. The lens 136 is a lens used to focus excitation light, e.g., an achromatic doublet lens or the like. A software program further controls the independent components of the TECCM apparatus 120 through a unified interface.

In one embodiment, the pipet positioning system 122 further includes a positioning system to extend the spatial range of the system 122. In another embodiment, the additional positioning system is an inchworm-type system. In another embodiment, the amplifier of the TECCM apparatus 120 is a patch-clamp amplifier and the TECCM apparatus includes a DAQ interface for computer control. In yet another embodiment, the software program is LABVIEW software.

Nothing in this disclosure should be construed to limit the materials that can be used with this embodiment. It is contemplated that the TECCM apparatus 120 is applicable in any electrochemical system, to any species which can be handled in solution, and can be configured to produce any desired spatial arrangement with spatial resolutions below 100 nm.

Figure 3A:
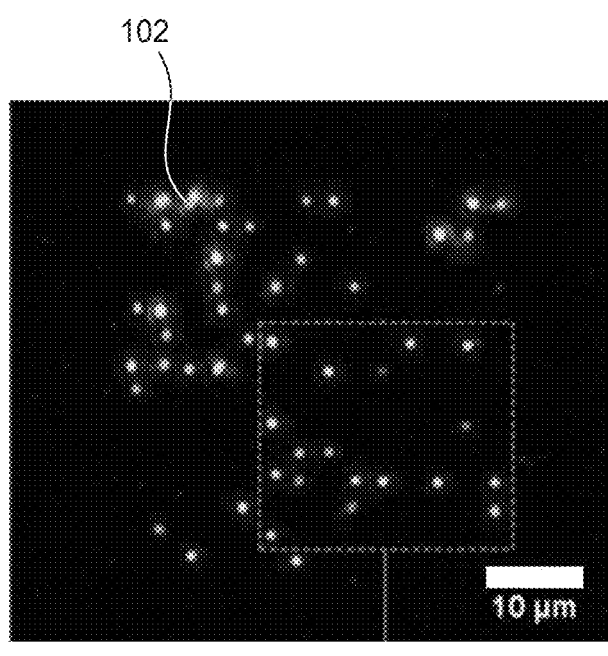
FIG. 3A illustrates an image of optical dark field scattering of Ag nanoparticle array distributed across a nanoparticle array on an indium tin oxide substrate according to an embodiment of the disclosure.
Figure 3B:
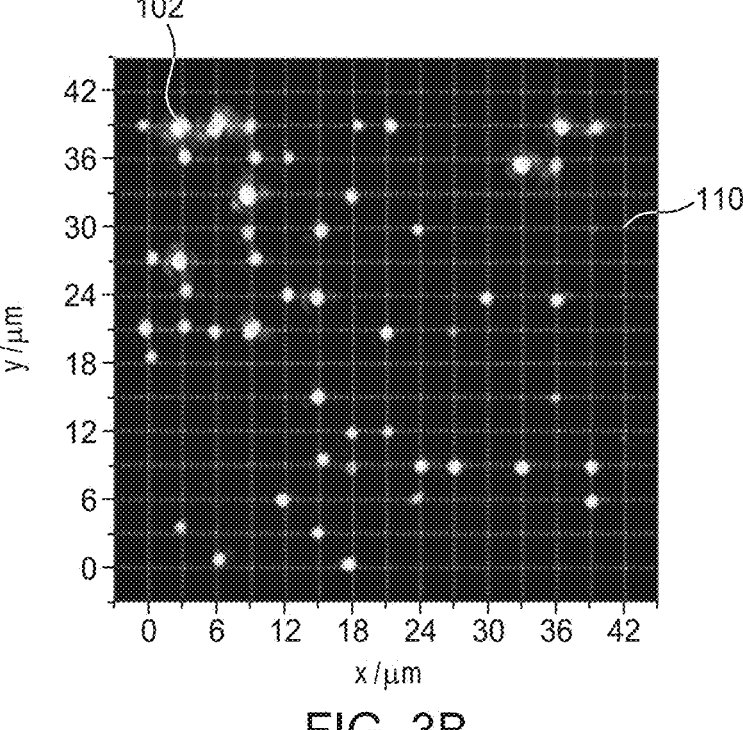
FIG. 3B illustrates the nanoparticle array of FIG. 3A according to an embodiment of the disclosure.
Figure 3C:
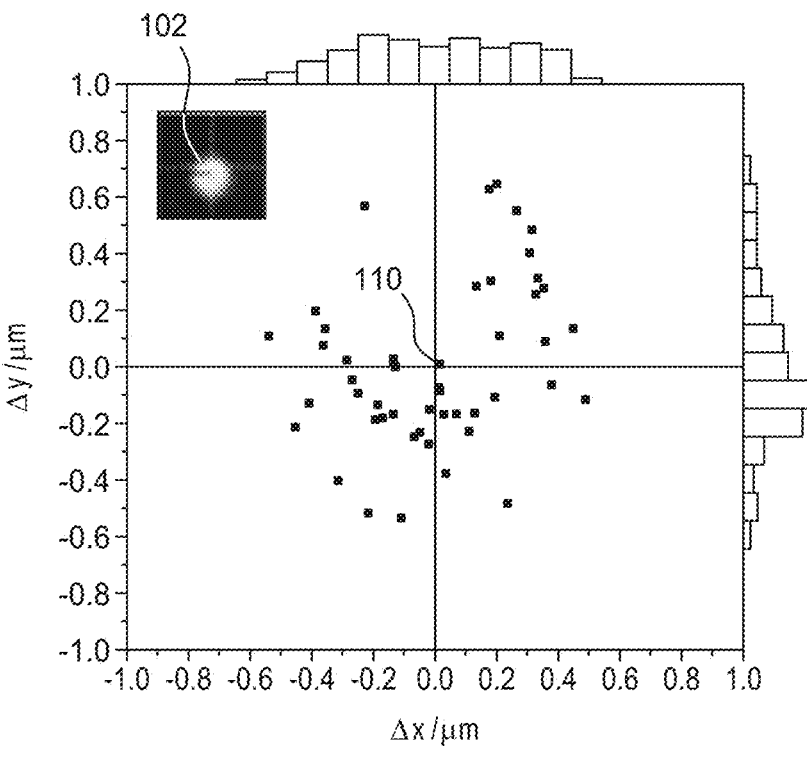
FIG. 3C illustrates a graph of placement accuracy analysis according to an embodiment of the disclosure.
Figure 3D:
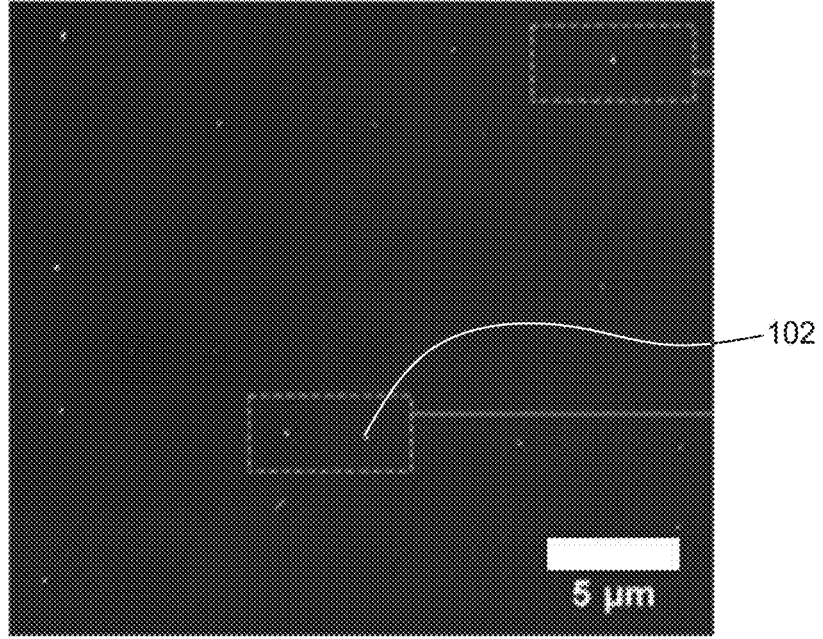
FIG. 3D illustrates a scanning electron microscopy image of the area indicated in FIG. 3C according to an embodiment of the disclosure.
Figure 3E:
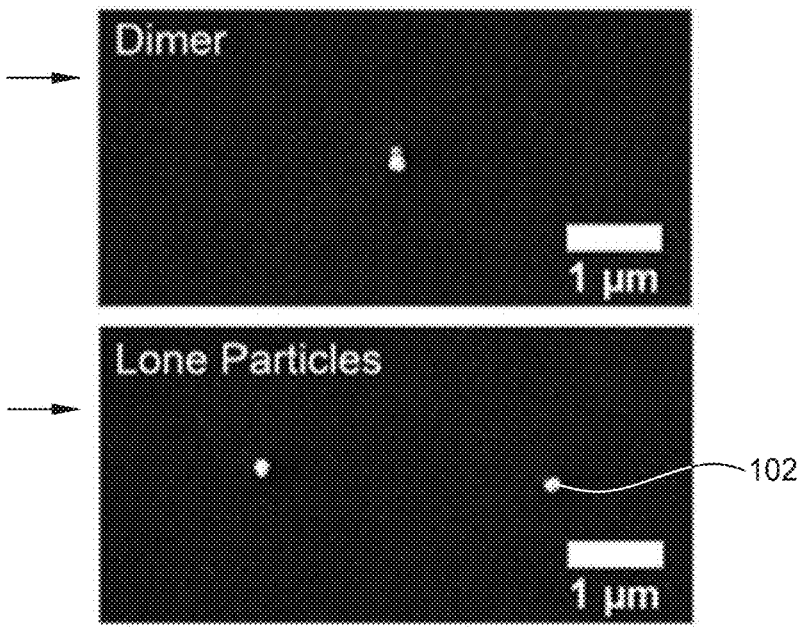
FIG. 3E illustrates high-resolution SEM images of the areas indicated in FIG. 3D according to an embodiment of the disclosure.
Figure 3F:
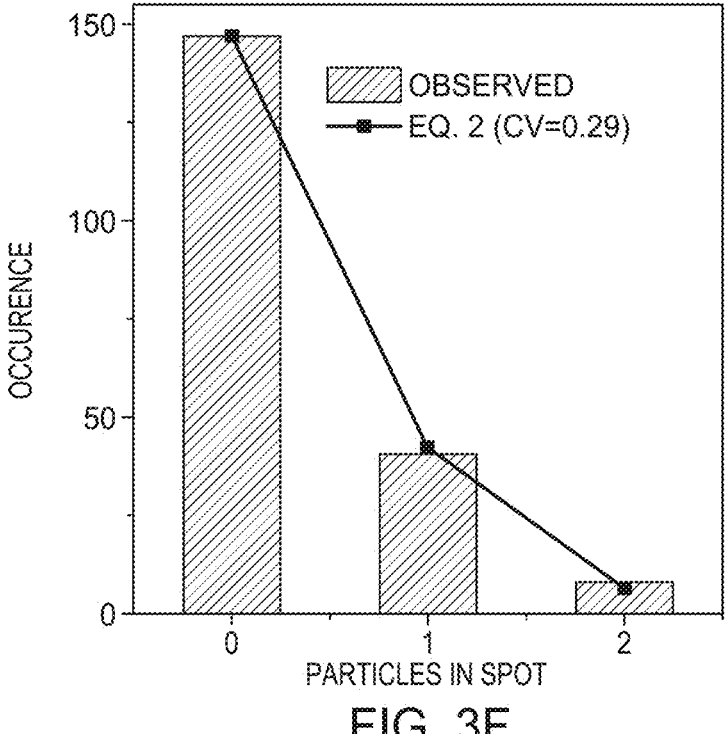
FIG. 3F illustrates a graph of the number of particles per spot in in the nanoparticle array according to an embodiment of the disclosure.

In one embodiment of the pipet-based approach 100, the nanoparticle 102 is consists of citrate-capped silver (Ag) nanoparticles. The Ag nanoparticles 102 were distributed across a 14 contact point×14 contact point array with 3 μm spacing using a 1.0 μm pipet 106. Referring to FIGS. 3A and 3B, optical imaging showed that the Ag nanoparticles 102 were distributed across ~25% of the contact points 110 (the intersections of the grid lines in 3B corresponding to the contact points). Referring to FIG. 3C, an analysis of the placement accuracy, generated by comparing the centroid of a 2D Gaussian fit to each contact location 110 shown in FIG. 3B is shown. Referring to FIGS. 3D and 3E, correlated Scanning Electron Microscope (SEM) measurements were carried out to confirm that these features in the area indicated in FIG. 3A were due to the Ag nanoparticles 102 and to determine the number of Ag nanoparticles at each site. As will be noted, the feature in the top right corner of FIG. 3D, after analysis, is determined to be a group of Ag nanoparticles, while the two features in the lower center of FIG. 3D is determined to be single Ag nanoparticles. Most sites correspond to single nanoparticles 102, as would be consistent with statistical predictions, described below. Referring to FIG. 3F, the observed number of particles per spot in in the nanoparticle array is shown. Analysis of the nanoparticle array 101 revealed that the nanoparticles 102 were radially displaced from the pipet 106 axis towards the edge of the solution droplet 112 at the corresponding contact point 110.

At low concentrations, the probability of a nanoparticle 102 being deposited with the solution droplet 112 obeys Poissonian statistics in equation (1):

$$P_n = \frac{(CV)^n e^{-CV}}{n!} \tag{1}$$

Where n is the number of nanoparticles 102 in a solution droplet 112 with volume V and concentration C. The probability of placing a single nanoparticle 102 is controlled by altering the entity concentration (C) or pipet size (V). $P_1$ reaches a maximum of 1/e when CV=1. Thus, while it is improbable to construct "perfect" arrays using the pipet-based approach described above, the resulting array consists of ~⅓ empty contact points 110, ~⅓ single nanoparticle 102 contact points, and ~⅓ larger groups of nanoparticles contact points. This limitation, however, can be overcome using active feedback mechanisms, described in further detail below.

Figure 4A:
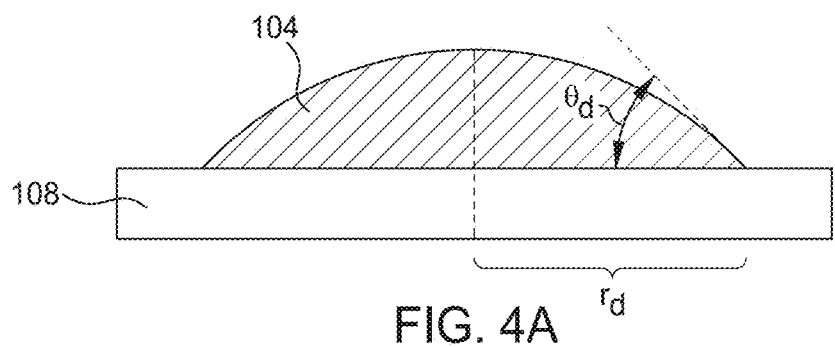
FIG. 4A illustrates a nanoparticle deposited on a substrate according to an embodiment of the disclosure.
Figure 4B:
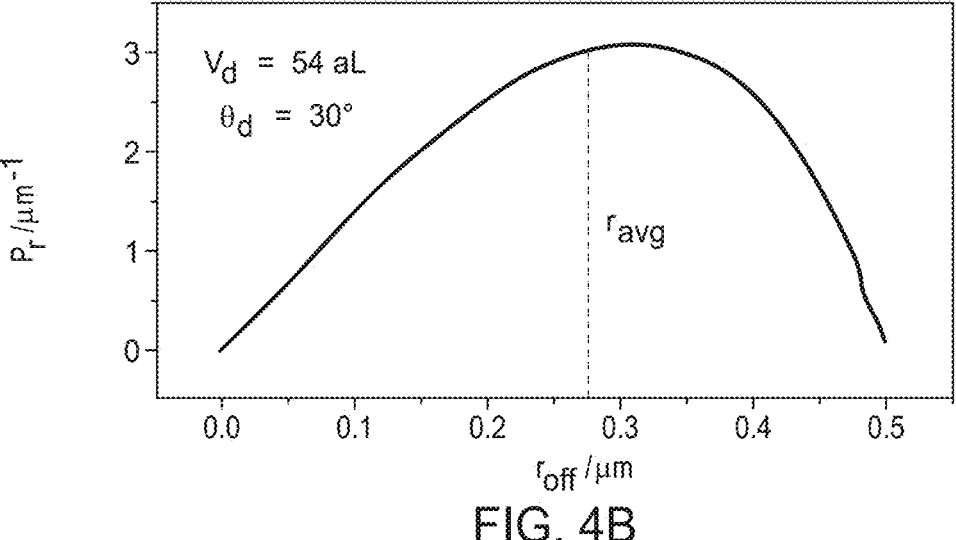
FIG. 4B illustrates the entity distribution in a solution droplet according to an embodiment of the disclosure.
Figure 4C:
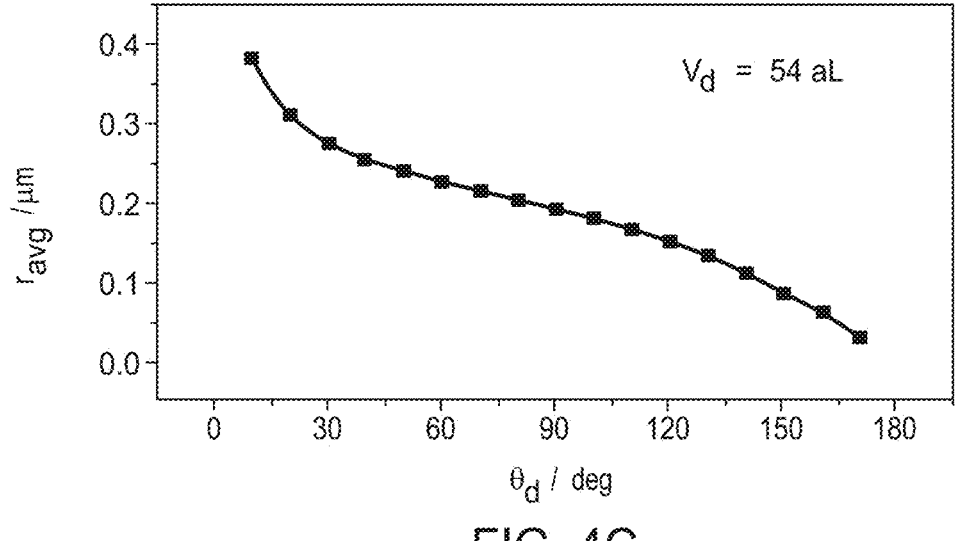
FIG. 4C illustrates the entity distribution in a solution droplet according to an embodiment of the disclosure.

The spatial distribution of nanoparticles is dictated, at least in part, by the accessibility of different regions of the substrate-droplet interface. The accessibility of the interface via diffusion is determined by the droplet geometry (contact radius and angle) depicted in FIG. 4A. Diffusion models are used to predict radial probability distributions ($P_r$) for nanoparticle attachment in this geometry, as illustrated in FIG. 4B. Based on these models, entities would be expected to adopt average radial positions, $r_{avg}$, of approximately 0.5-0.75 times the droplet contact radius, rd. For a constant droplet volume, $r_{avg}$ is expected to shift to smaller values with increasing contact angles (FIG. 4C), which indicates the spatial distribution of nanoparticles can be controlled via surface chemistry.

In another embodiment of the pipet-based approach 100, the pipets 106 utilized in the deposition are quartz pipets, and the substrate 108 is indium tin oxide. In particular, commercially available indium tin oxide ("ITO")-coated coverglass substrates are employed as optically-transparent electrodes. Pipets 106 are fabricated with various geometries and characteristics. Other substrates beyond indium tin oxide are also contemplated to be within the scope of this disclosure. The surfaces of these substrates 108 can be altered as desired utilizing known chemistries for ITO (e.g., phosphonic acid derivatives). The nanoparticles 102 employed can be commercially-available fluorescent polystyrene nanoparticles or metallic nanoparticles, depending on the optical measurement scheme.

In one embodiment, pipets 106 with diameters between 100 nm and 10 μm are utilized to deliver ~50 nm diameter citrate-capped gold (Au) or silver (Ag) nanoparticles onto ITO surfaces terminated with the native oxide (hydrophilic), alkane monolayers (hydrophobic), or charged monolayers (ammonium or carboxylic acid terminations). Droplets are deposited, rinsed, and dried before optical localization experiments are carried out, as seen in FIGS. 3A-3E. This process is accurate to less than 10 nm and the data can be used to construct radial placement distributions for comparison to theoretical predictions.

Figure 5A:
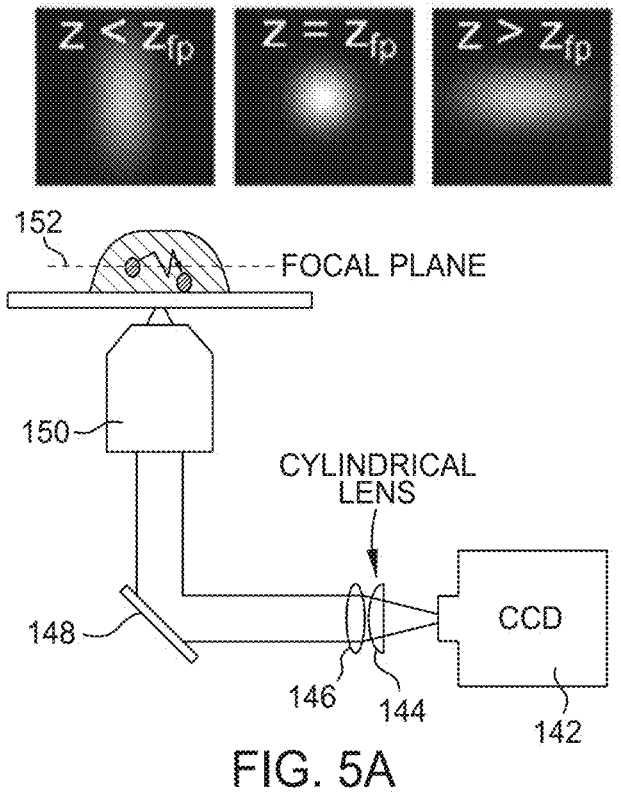
FIG. 5A illustrates a super-resolution optical imaging system according to an embodiment of the disclosure.
Figure 5B:
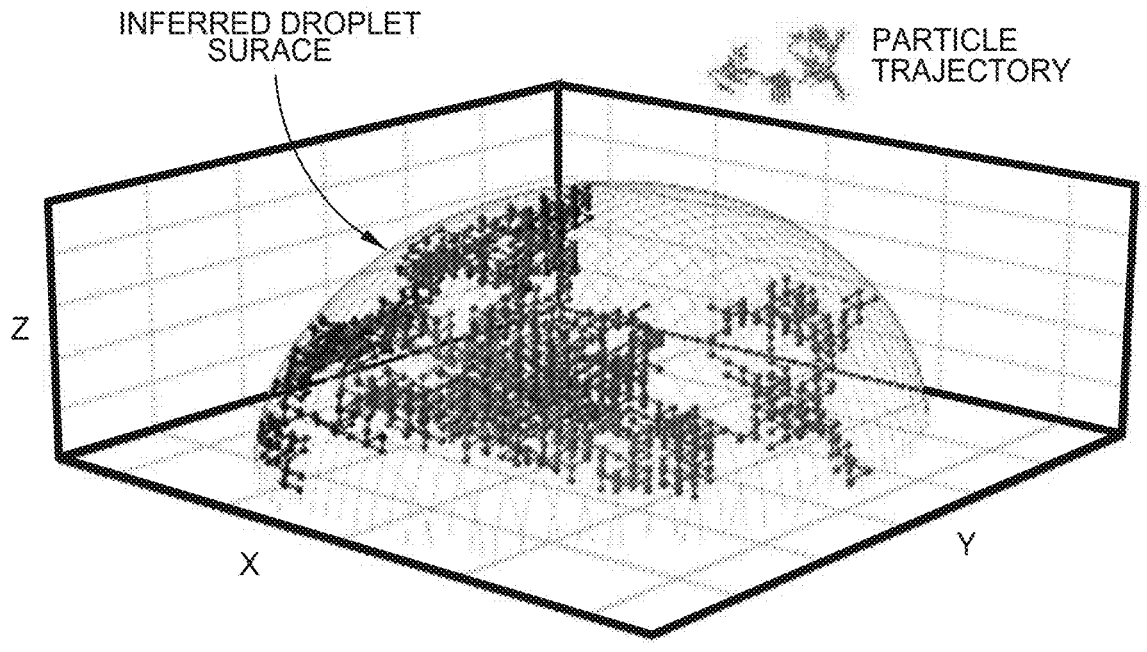
FIG. 5B illustrates a graph of 3D super-resolution imaging of droplet geometry according to an embodiment of the disclosure.

Referring to FIG. 5A, in some embodiments of the pipet-based approach, solution droplet 112 geometry is characterized via a super-resolution optical imaging system (SROIS) 140. The SROIS 140 includes a CCD 142, a first and second cylindrical lens 144, 146, a mirror 148, and a microscope 150. The SROIS 140 projects light through the first and second cylindrical lenses 142, 144, of the mirror 146, and through the microscope 148. This allows the CCD 142 to see the location of the nanoparticle 102 when it is in a focal plane 152. The geometry of solution droplets 112 created during the nanoparticle 102 deposition process is directly interrogated using super-resolution optical techniques from the SROIS 140. In some embodiments, fluorescent polystyrene nanoparticles 102 are used as the deposited entities. Solution droplets 106 are deposited under controlled, H$_2$O-saturated atmospheres in order to prevent evaporation. Referring to FIG. 5b, astigmatism-based 3D fluorescence localization techniques of the SROIS 140 are employed to track the movement of nanoparticles 102 within solution droplets 112. Solution droplet 112 geometries are inferred as surfaces enclosing the translational trajectories of nanoparticles 112 move within the solution droplets.

In another embodiment of the pipet-based approach 100, active feedback mechanisms can be utilized for nanoparticle 102 placement within solution droplets 112. While placing single nanoparticles 102 within solution droplets 112 in a random fashion should have a maximum success rate of ~⅓, dictated by Poissonian statistics, active feedback mechanisms can overcome this limitation by indicating whether nanoparticles are present.

Figure 6:
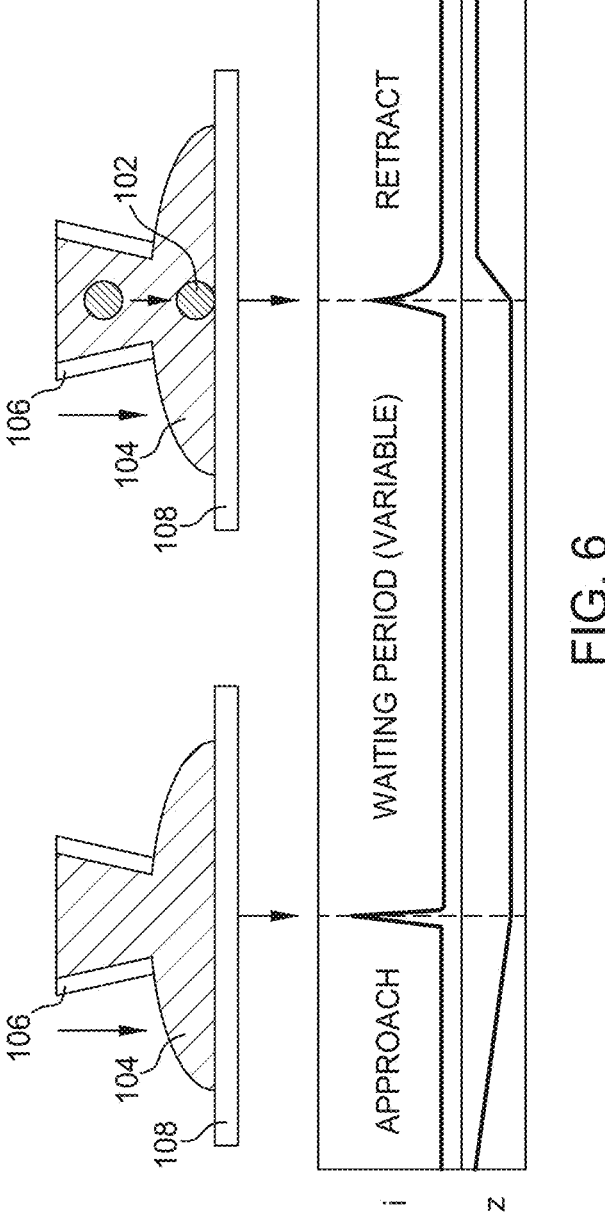
FIG. 6 illustrates a schematic of active detection of entity placement according to an embodiment of the disclosure.

Referring to FIG. 6, a first method of active detection of entity placement is shown. A potential is applied to the substrate 108 to drive the migration of nanoparticles 102 toward the substrate. The substrate 108 can then detect signals associated with the passage of nanoparticles 102 through the pipet 106 tip, such as resistive pulses or faradaic signals arising from substrate-nanoparticle contact. The application of potential enables nanoparticles 102 to be placed on the substrate 108 with success rates approaching 100%.

Figure 7B:
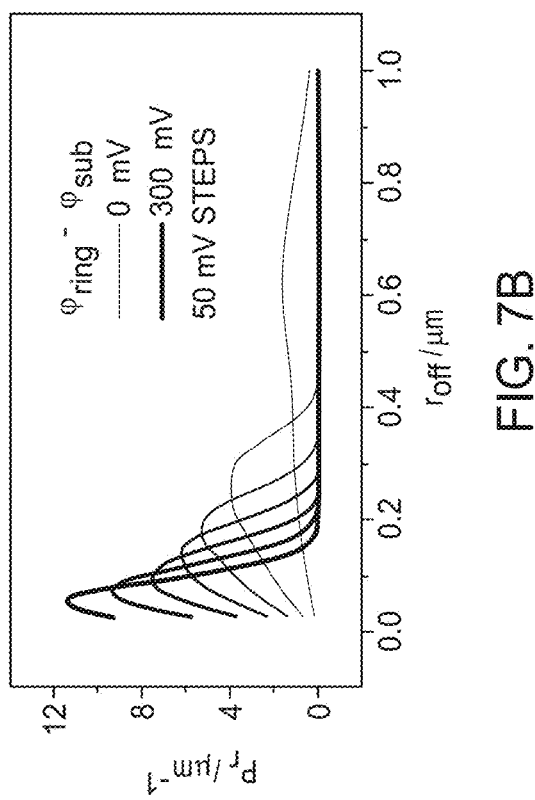
FIG. 7B illustrates a meniscus drop biased over a range of voltage increments by a ring electrode according to an embodiment of the disclosure.
Figure 7A:
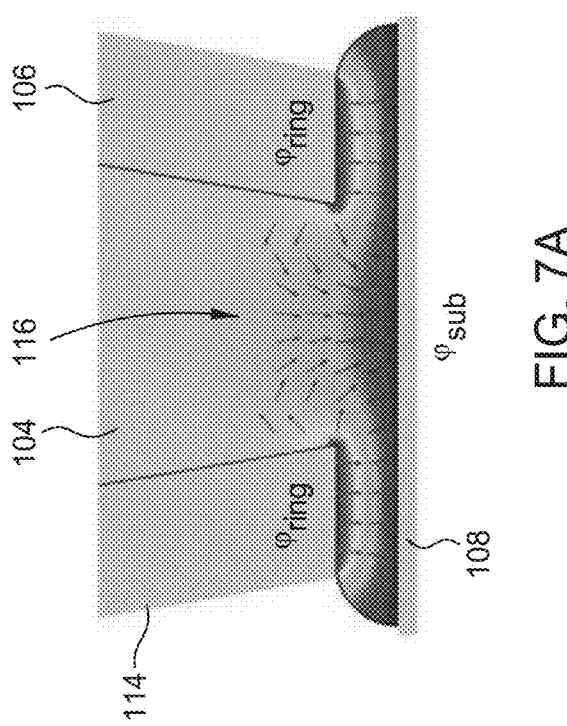
FIG. 7A illustrates a schematic for entity delivery under controlled fields at the pipet tip according to an embodiment of the disclosure.

Referring to FIG. 7A, another method of an active feedback mechanism for the pipet-based approach 100 is shown. Spatial control of nanoparticle 102 placement in the pipet-based approach 100 is dictated by the size of the solution droplets 112 created upon pipet 106 contact with a substrate 108, and is ultimately comparable to the terminal diameter of the pipet employed. While placement accuracies of 250-500 nm can be sufficient for the application of the TECCM apparatus 120, it is desirable to achieve higher accuracies for other applications of the pipet-based approach 100. For charged entities, a pipet 106 is fabricated with a ring electrode 114 disposed at its tip to enable thermal evaporation. By controlling the potential applied to the electrode 114, electromagnetic fields 116 are generated to focus nanoparticles toward substrate 108 via migration to a small region centered within the pipet 106. Referring to FIG. 7B, a 1 μm diameter probe and a 2 μm meniscus drop is shown being biased over a range of 0 to 0.3 V at 0.05 V increments by a ring electrode. Typical diffusion coefficients and zeta potentials (i.e., mobilities) indicate the fabricated pipet 106 achieves delivery confined to less than a tenth of the pipet radius. In order to achieve this result, the electrode has a thickness of at least 10 nm, but the thickness not greater than about ⅒ of the pipet 106 diameter. The ring electrode 114 is fabricated from gold, platinum, or other inert metals. It is contemplated to be within the scope of this disclosure that the pipet 106 may be effective for other particles beyond those described herein. These active feedback mechanisms, pipet/droplet geometries, and applications of electrical fields are effective in influencing spatial distribution of nanoparticle 102 placement and enable high-throughput, targeted single-nanoparticle analyses. In another embodiment of the pipet-based approach, a dual-barrel pipet may be used to deliver nanoparticles 102 to the substrates 108. The double-barrel pipet enables the detection of pipet contact via an ionic current flowing between the barrels and enables the use of unbiased, or even insulating substrates 108. As a result, undesirable reactions at the substrate 108 or the nanoparticles 102 as a result of the applied potential is avoided.

It is desirable to develop an on-demand protein biosensor platform for continuous monitoring in biomanufacturing applications. Current experimental approaches are not guaranteed to produce proteins with the necessary properties, and typically require a long time to fabricate and incur high costs. The benefits of the platform and embodiments described herein can be realized through the deployment of biosensors for insulin and IL-6, two protein analytes with high importance and potential for impact in biomanufacturing. The methods and protocols to fabricate nanoparticle arrays can be developed based on SECCM techniques. The methods described herein enable improved reproducibility in the design of functional surfaces.

Secreted proteins such as insulin and interleukin-6 (IL-6) are the natural signals that cells, tissues, and organs use to report out on their status and needs to other physiological systems. While nature has evolved a vast repertoire of molecular tools to link the physical recognition (binding) of specific molecules to the transduction of a signal and the coordination of appropriate responses, the conditions of industrial processes preclude the use of the vast majority of nature's biosensors. The cell-to-cell and batch-to-batch variability inherent to biological systems presents further challenges for process standardization and control, underscoring the value of simultaneous monitoring of multiple parameters. Embodiments described herein utilize sensors and manufacturing methodologies for the direct, specific, dynamic, and real-time detection of such biological signals in commercial or industrial processes.

Insulin is a secreted protein growth factor central to the regulation of glucose and amino acid metabolism. Insulin is both a biomanufacturing product as a biologic drug and an analyte monitored in the manufacture of certain cells and tissues.

IL-6 is a secreted signaling protein with roles in immune response, inflammation, metabolism, cancer, organ growth and development, and the central nervous system. IL-6 often serves as a "warning signal" in the event of damaged, dying, or infected cells.

Figures 8A, 8B, 8C:
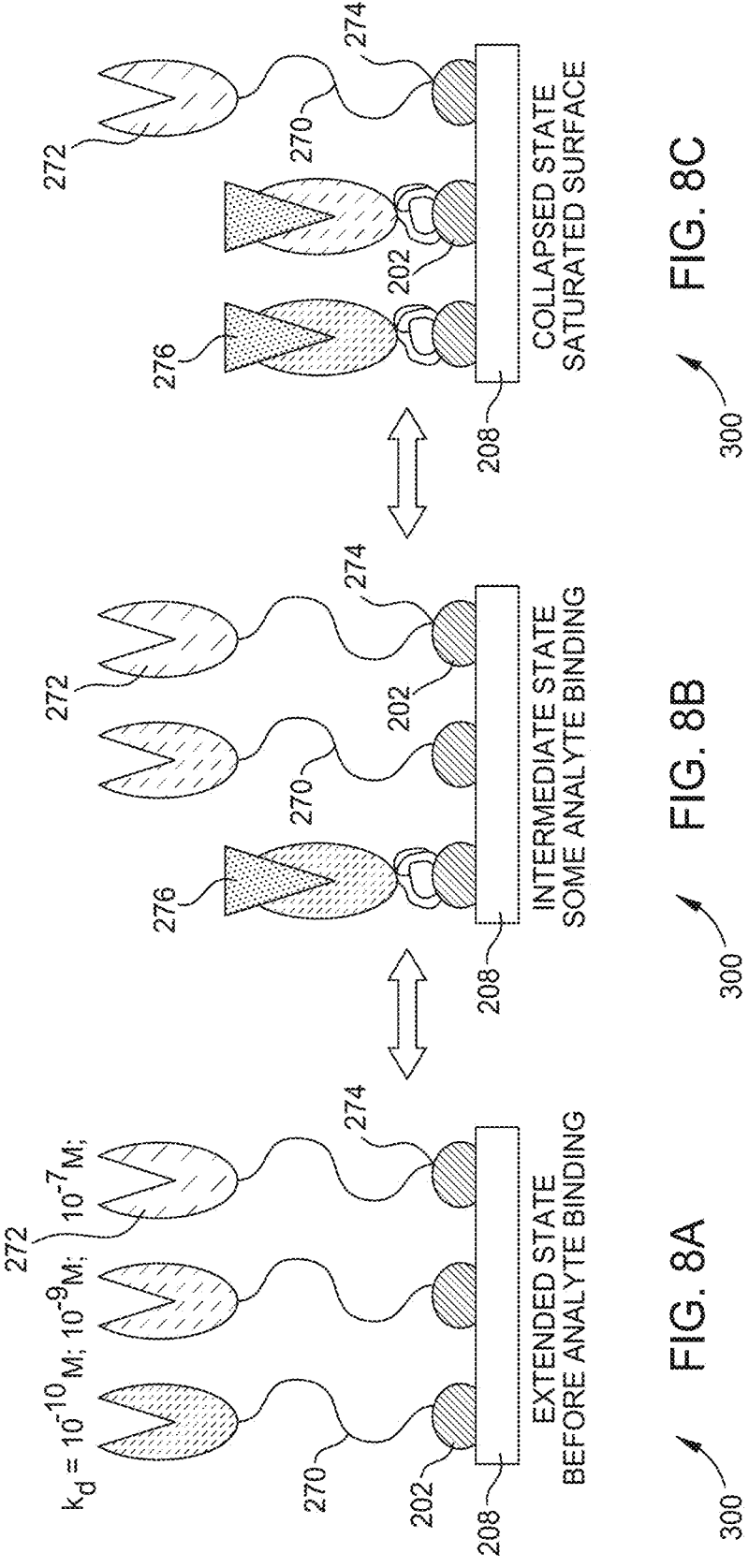
FIG. 8A illustrates a schematic of a biosensor in a first conformation according to an embodiment of the disclosure.
FIG. 8B illustrates a schematic of a biosensor in a second confirmation according to an embodiment of the disclosure.
FIG. 8C illustrates a schematic of a biosensor in a third conformation according to an embodiment of the disclosure.
Figure 9:
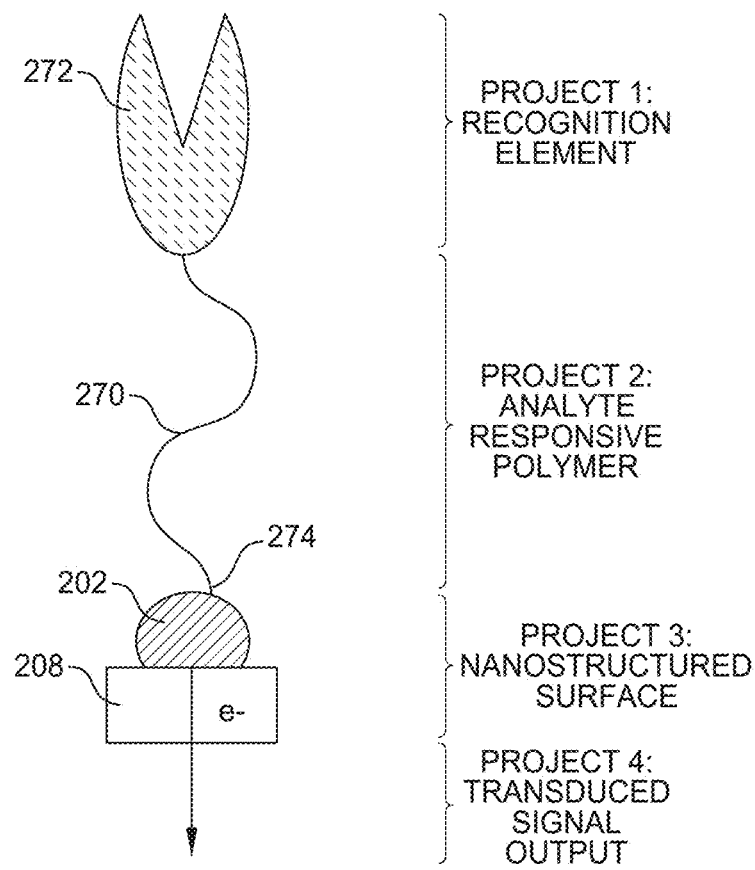
FIG. 9 illustrates a functionalized nanoparticle according to an embodiment of the disclosure.

Referring to FIGS. 8-9, a biosensor for monitoring surface binding events is generally indicated at 300. The biosensor includes nanoparticle array 201 and an analyte responsive polymer (ARP) 270. The nanoparticle array 201 further includes a plurality of nanoparticles 202, and the ARP 270 further includes a recognition element 272 at a first end of the ARP 270 and a terminus 274 at a second end of the ARP270 distal to the first end of the ARP 270. Referring specifically to FIGS. 8A-C, a plurality of nanoparticles 202 are configured to be distributed across the nanoparticle array 201 at a plurality of contact points 210 on a substrate 208. At FIG. 8A, the terminus 274 of ARP 270 is configured to conjugate to the each of the nanoparticles 202 in the nanoparticle array 201, thus creating a "binding-end-out" orientation for the recognition elements 272. Referring to FIGS. 8B and C, the recognition element 272 is configured to react with an analyte 276. FIG. 8B illustrates the intermediate state where there is some analyte binding, while FIG. 8C illustrates the collapsed state where the nanoparticle array 201 is saturated. The reaction of the recognition element 272 with the analyte 276 creates a change in the electrochemical signal at the surface of the nanoparticle 202 by obstructing media flow around the nanoparticle 202. The nanoparticle 202, acting as an electrode for the sensor, then transmits this change in electrochemical signal to the sensor in order to monitor surface events of the ARP 270.

In one embodiment, the sensor enabled in the biosensor 300 is and electrochemical impedance spectrometer and the signal generated by the surface events is a reproducible Electrochemical Impedance Spectroscopy (EIS) signal. The signal is used to monitor the binding-unbinding events between the surface bound recognition elements 272 and can be amplified based on the conformational change of the nanoparticle 202 surface-bound ARP 270.

Figure 10:
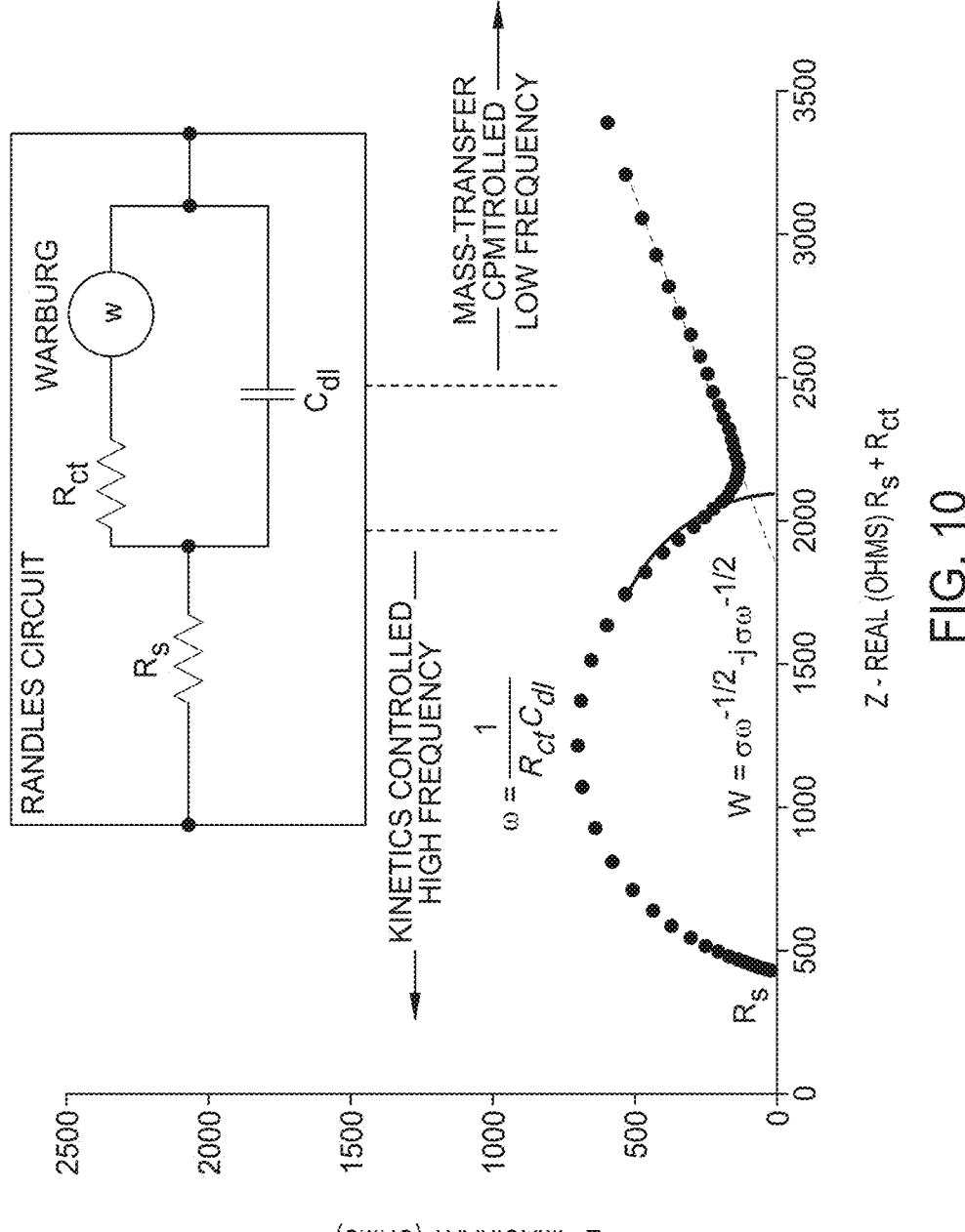
FIG. 10 illustrates a Nyquist plot with a Randles circuit used to interpret data according to an embodiment of the disclosure.

EIS is responsive to the interface between an electrode and an analyte solution. EIS is the application of different alternating voltage frequency while measuring the current response equivalent to the electrons flowing through the system. Referring to FIG. 10, the resulting data is represented as impedance on a Nyquist plot, where the real (in-phase) and imaginary (out-of-phase) components are displayed separately. Analysis of the impedance data is interpreted by modeling the electrode-solution interface as an equivalent circuit; the Randles circuit is the most common model, containing a solution resistance ($R_s$), charge-transfer resistance ($R_{ct}$), diffusive Warburg impedance (W), and double-layer capacitance ($C_{dl}$).

EIS is utilized to track small changes on the surface of the nanoparticle 202 and can be utilized to demonstrate biosensor 300 functions in situ. Analyte 276 binding events or conformational changes increase coverage of the nanoparticle 202 surface, thereby hindering and blocking the transfer of electrons across the nanoparticle surface interface and resulting in an increase in Ret. Default EIS settings are utilized, which are measurements in buffered solution (non-faradaic EIS) with a 5 mV AC oscillating potential around a 0 V DC offset vs. open circuit potential, which are further optimized for each specific case. However, this should not be construed to limit the scope of the disclosure, as other settings are anticipated by this disclosure.

In alternate embodiments, the nanoparticle 202 surfaces can be modified with either the recognition element 272 or the analyte responsive polymers 270. Surfaces can be confirmed with x-ray photoelectron spectroscopy (XPS), atomic force microscopy (AFM), and attenuated total reflectance Fourier transform infrared (ATR-FTIR). Using EIS and eQCM, the conjugation and removal of the analyte 276 from the nanoparticle 202 surface are monitored. Serial dilution is used to determine the range and sensitivity of the sensor; ten different analyte concentrations were tested: $0.00K_d$, $0.01K_d$, $0.05K_d$, $0.1K_d$, $0.5K_d$, $1.0K_d$, $5K_d$, $10K_d$, $50K_d$, $100K_d$. Data was collected in triplicate and analyzed to determine sensitivity and linear dynamic range. Temperature cycling of the surface-bound ARP 270 determine the temperature dependency of the kinetic parameters.

In one embodiment, the biosensor 300 monitors surface binding events without tags (e.g. electrochemical, optical) or enzymes. Currently, conventional transduction methods of in-line electrochemical protein biosensors require tagging the nanoparticle 202 surface motif with an active electrochemical signal to monitor analyte response with voltammetry and amperometry. The ability to electrochemically monitor binding events without an active electrochemical tag increases capabilities in the development of biosensors.

Figure 11:
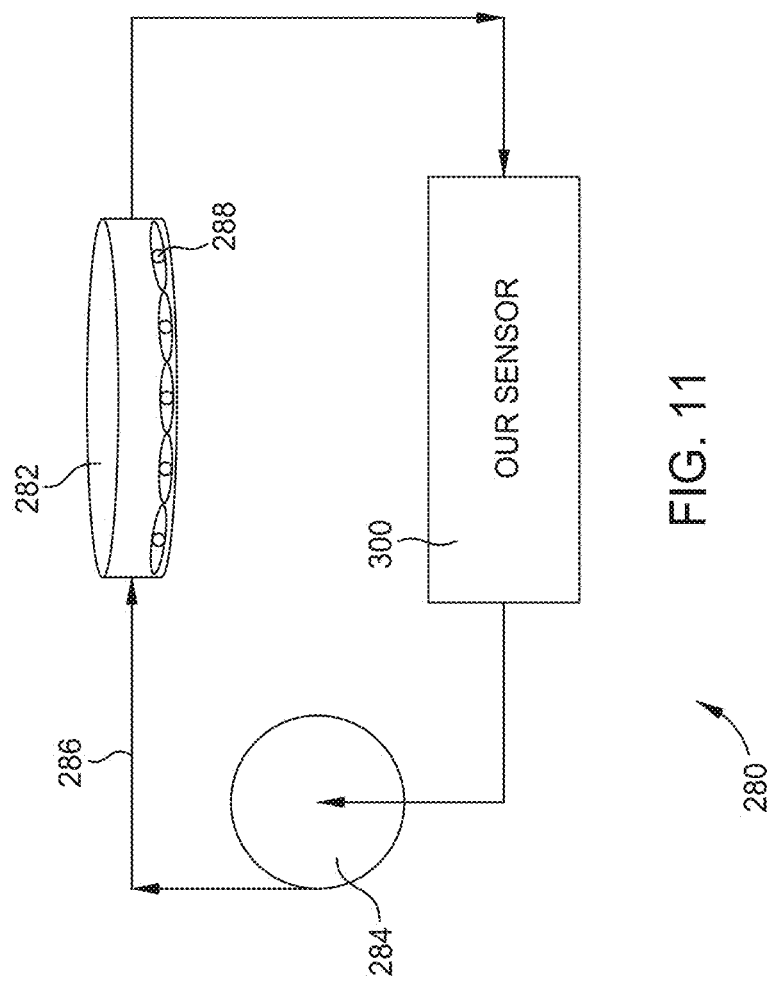
FIG. 11 illustrates an in situ sensor system according to an embodiment of the disclosure.

Referring to FIG. 11, an in situ sensor system 280 is shown. The in situ sensor system includes a bioreactor 282, the biosensor 300, a peristaltic pump 284, and tubing 286. Cells 288 used for biosensor 300 sensing can be grown in the bioreactor 282. The tubing 286 returns and removes media containing the cells 288 to and from the biosensor 300. The peristaltic pump 284 can control the flow rate of the media being transferred between the cells and the sensor.

The EIS signal output is used to demonstrate sensor function in situ of cell growth. Two different cell lines, bone marrow-derived mesenchymal stem cells which secrete IL-6, and stem cell-derived pancreatic islets which secret insulin, in particular, were utilized for testing according to embodiments of the present disclosure. Monitoring the media of these two cell lines provides validation of long-term in-situ sensor use for continuous monitoring of the effluent of the cells.

In one embodiment, the in situ sensing system 280 is utilized to measure IL-6 continuously and accurately. The recognition element 272 of the ARP 270 is configured to react with IL-6 in situ in order to monitor end-of-life for dying tissues. The biosensor 300 measures the cells 288 over the period of 8 days at intervals of 1 hour (192 measurements) within 5% error to traditional ELISA sensors taken every two days (4 measurements). Through spiking of media, an increase and decrease of the target analyte 276 may be identified.

In one embodiment, the in situ sensing system 280 is utilized to measure insulin in-line continuously and accurately. The recognition element 272 of the ARP 270 is configured to react with insulin in situ in order to determine when a pancreatic islet is mature for tissue engineering practices. The biosensor 300 measures the cells 288 over the period of 8 days at intervals of 1 hour (192 measurements) within 5% error to traditional ELISA sensors taken every two days (4 measurements). Through spiking of media, an increase and decrease of the target analyte 276 may be identified.

Nothing in this disclosure, however, should be construed to limit the scope of the disclosure to mesenchymal stem cells or stem cell derived pancreatic islets, as other cell lines, i.e., *E. coli* and CHO, may be utilized. In addition, other time periods and testing intervals are also contemplated by this disclosure.

Figure 12:
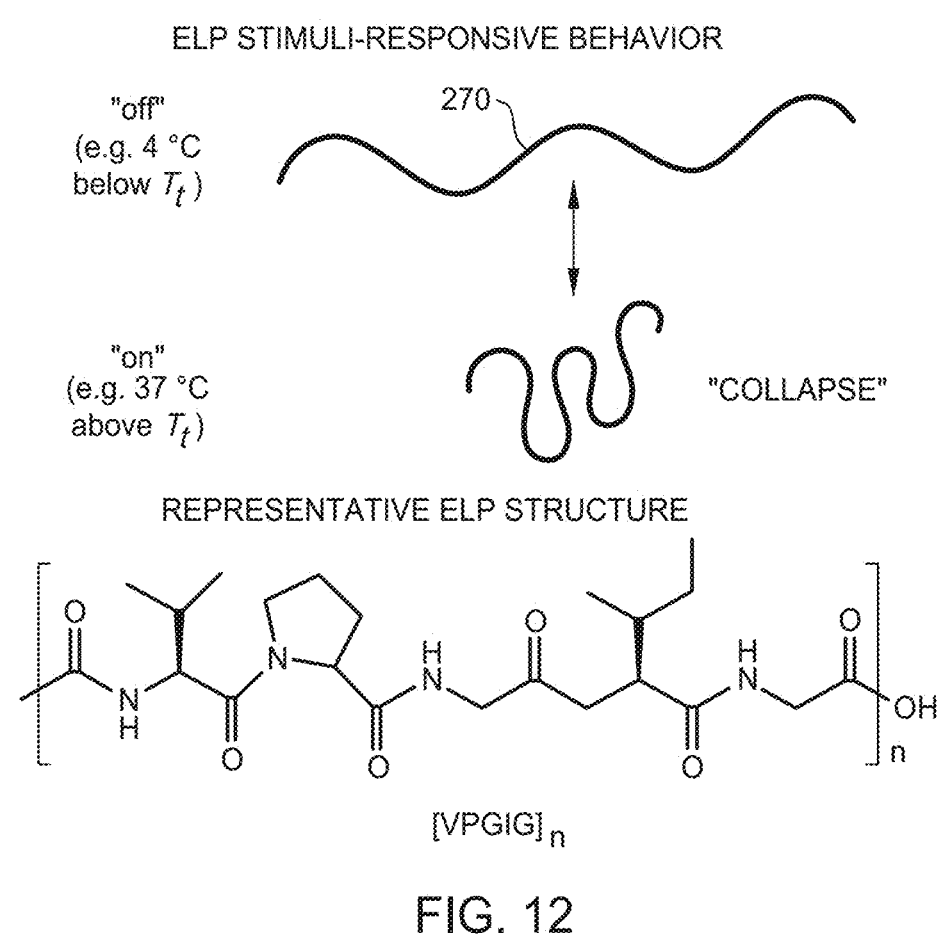

In one embodiment of the biosensor 300, the nanoparticles 202 are comprised of gold nanoparticles and the ARPs 270 are comprised of elastin-like polymers (ELPs). ELPs are genetically engineered polymers whose behavior is dictated by a defined DNA sequence. They are stimuli-responsive, "smart" polymers based on amino acid sequences derived from the natural protein elastin. ELPs exhibit a reversible "inverse" temperature transition, existing as a soluble monomer before the transition temperature $T_t$ and becoming more ordered and, in solution, self-assembling into micro-scale coacervates with increasing temperature. This enables site-specific positioning of reactive functional groups such as amines, carboxylates, and thiols provided by the diverse repertoire of amino acids. The basic repeating unit of ELPs is a pentapeptide repeat referred to as VPGXG, where V=valine, P=proline, G=glycine, and X=any amino acid except proline, as illustrated in FIG. 12. The precise control of overall polymer length and polarity enables tuning of the transition temperature ($T_t$) of the ELP, the temperature above which ELPs will undergo hydrophobic collapse and aggregation in solution. This hydrophobic collapse results in increased coverage of the nanoparticle 202 surface, thereby hindering and blocking the transfer of electrons across the nanoparticle surface interface.

In another embodiment, a suite of candidate ELP backbones that vary in length and mole fraction of hydrophobic and hydrophilic guest (X) residues have been produced. The designed ELPs also contain a unique cysteine residue near their N-terminus enabling end-tethering to the Au surface via gold-thiol attachment. For instance, ELPs can be produced in *E. coli* and purified to homogeneity as evaluated by polyacrylamide gel electrophoresis (SDS-PAGE) before surface-immobilization.

Figure 13:
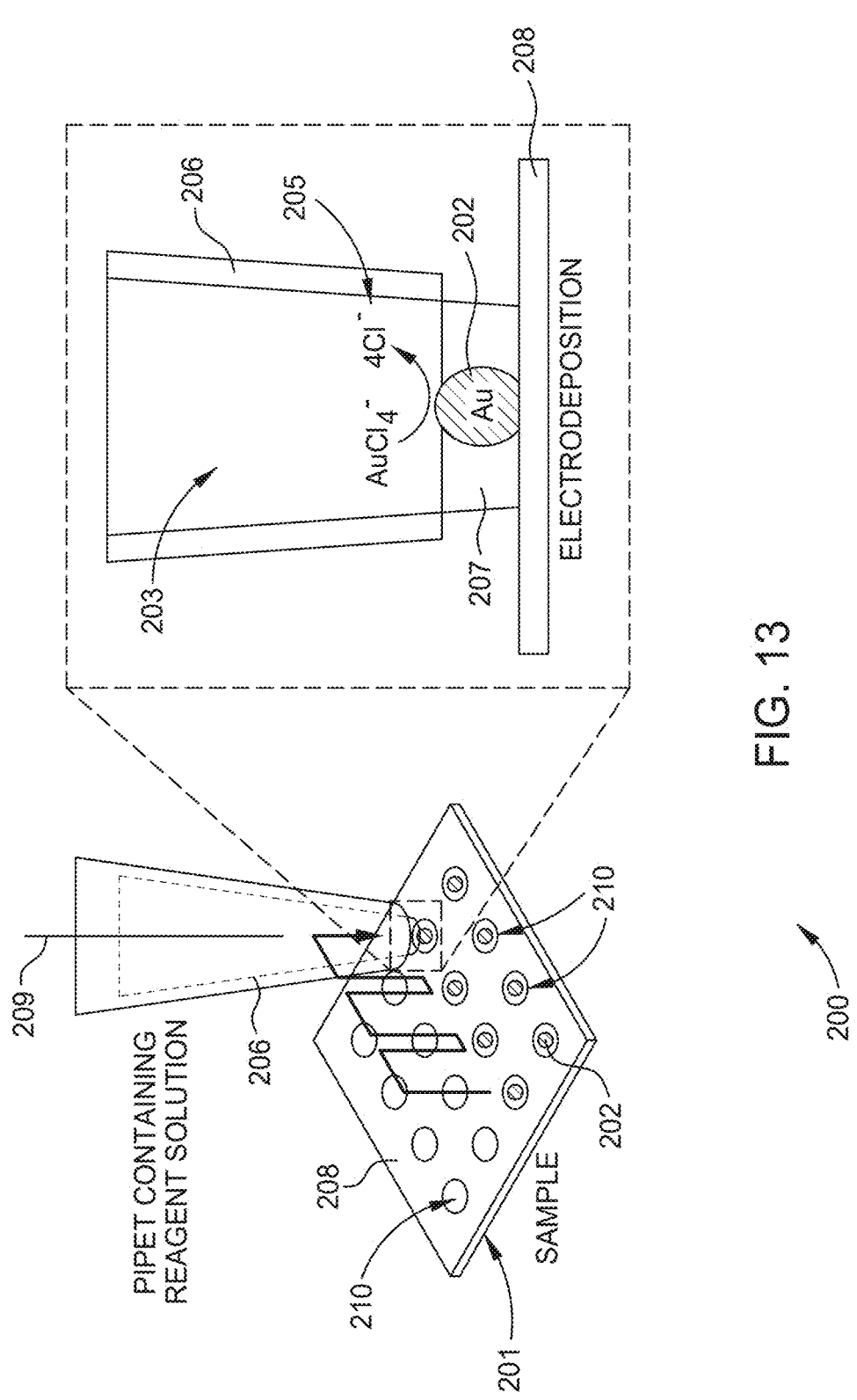
FIG. 13 illustrates a schematic of fabricating a nanoparticle array though electrodeposition according to an embodiment of the disclosure.
Figure 14:
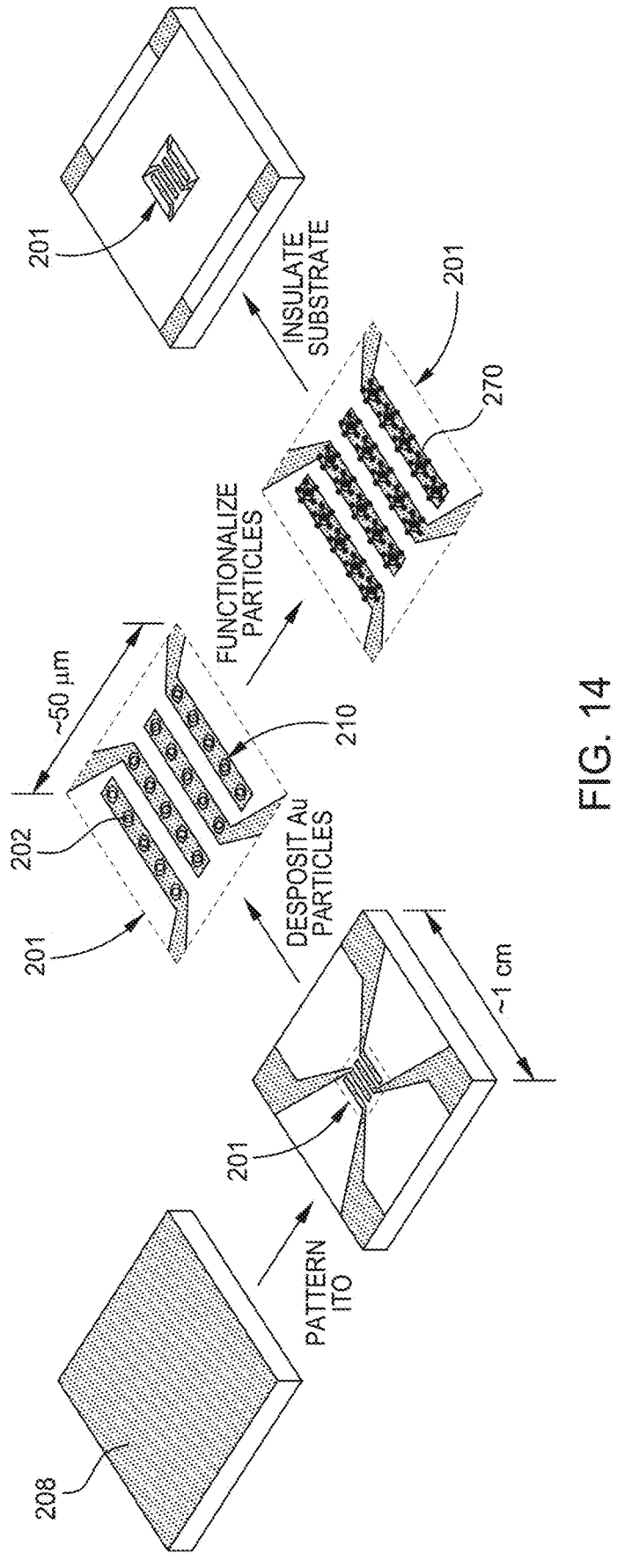
FIG. 14 illustrates a schematic for fabricating a biosensor according to an embodiment of the disclosure.

FIGS. 13-14 illustrate an exemplary method of fabricating a nanoparticle array 201 to be used in a biosensor 300, generally referred to as reference numeral 200. Spatial control over the morphology and surface chemistry of heterogeneous interfaces is required to achieve reliable, multiplexed electrochemical sensing. Existing methods for the fabrication of these interfaces cannot achieve of a high degree of control, significantly limiting the development of effective sensing platforms. The electrochemical methods described herein can be employed to fabricate nanoparticle arrays 201 of nanoparticles 202 and selectively modify each nanoparticle with desired chemical recognition elements 250, yielding highly reproducible nanoparticle arrays with electrode surfaces for biosensing applications. An electrochemical method for fabrication of nanoparticle arrays 201 includes functionalization of the nanoparticle arrays with recognition elements 272 and can be deployed as a biosensor for, among other things, biological applications.

The electrochemical approach to fabricating a nanoparticle array 201 comprises forming a solution 207 containing a material precursor 203 and an electrolyte 205 and loading the solution into a pipet 206. The nanoparticles 202 are fabricated using Scanning ElectroChemical Cell Microscopy (SECCM), a pipet-based electrochemical microscopy technique. The method includes inserting a wire 209 into the solution 207 to serve as a counter electrode and bringing the pipet into brief contact with the substrate 208. The small, electrolyte filled pipet 206 is employed to locally address a surface and drive reaction locally. Next, the method includes applying an electrical bias the substrate 208 and the wire 209 and forming a nanoparticle 202 via electrodeposition. Two step potential waveforms are employed to control the nanoparticle 202 nucleation and growth processes independently: a large amplitude nucleation operation to create a single particle within the contact point 210 and a longer time, and small amplitude growth operation to reach the desired size. The size of the deposited nanoparticle 202 is controlled by terminating the application of the growth potential once the desired amount of charge has passed. Next, the method consists of repeating the steps of bringing the pipet 206 into brief contact with the substrate 208, applying an electrical bias between the substrate and the wire 209, and forming a nanoparticle 202 via electrodeposition across an array of contact points 210 to create the nanoparticle array 201. Finally, the method includes rinsing the substrate 208 with a solvent 204 to remove residual electrolyte 205.

In one embodiment of the pipet-based approach 100, the TECCM apparatus 120 is enabled. As described above, the TECCM apparatus 120 is based on correlated optical and electroanalytical measurements and is used to fabricate ordered arrays of nanoparticles 202. The pipet positing system 122 controls the x, y, and z, position of the pipet 206 with respect to the substrate 208. The first and second piezos 122a, 122b are used to locally address the pipet 206 to the substrate 208 with the solution containing the material precursor 203 and the electrolyte 205. The first piezo 122a brings the pipet 206 into contact with the substrate 208 and detects the contact through a pressure induced electrical output of the first and second piezo. Once in contact, the TECCM apparatus 120 controls the applications of potential waveforms for electrodeposition. When the desired amount of charge has reached been passed, the first and second piezo 122a, 122b release the contact between the pipet 206 and the substrate 208, leaving deposited nanoparticle 202. Using the microscope objectives 126, 136, the TECCM apparatus 120 can monitor the growth of the nanoparticle 202. A software program further controls the independent components of the TECCM apparatus 120 through a unified interface.

In one embodiment, the TECCM apparatus 120 pipet 206 can be approached to the substrate 208 under the application of an anodic bias. Pipet-substrate contact is detected as an anodic current spike. The multi-operation cathodic potential waveform is applied to drive particle deposition, and the growth operation is terminated when the desired charge has passed, as described above. The pipet 206 is then retracted and moved the next contact point 210.

In one embodiment, the pipet positioning system 122 further includes a positioning system to extend the spatial range of the system. In one embodiment, the additional positioning system is an inchworm-type system. In another embodiment, the electric system includes a patch-clamp amplifier and a DAQ interface for computer control. In another embodiment, the software program is LABVIEW software.

In one embodiment, the pipet has a diameter of ~500 nm, the material precursor is HAuCl$_4$ and leads to the fabrication of gold (Au) nanoparticles 202, as seen in FIG. 13. In one embodiment, the wire 209 is a gold wire. Ordered nanoparticle arrays 201 of Au nanoparticles can be reproducibly fashioned and each nanoparticle 202 can be selectively modified using Scanning ElectroChemical Cell Microscopy (SECCM), yielding highly reproducible electrode surfaces for biosensing applications. Fabrication techniques can be developed and validated for producing arrays of hemispherical Au nanoparticles 202 on conducting substrates 208. It is believed that methods for the selective functionalization of nanoparticles 202 within the ordered nanoparticle arrays 201 of AU nanoparticles with different sensing elements can be fabricated. Sensors described herein selectively probe the concentration of analytes 276 within complex biological matrices in a selective, reproducible manner.

Figure 15A:
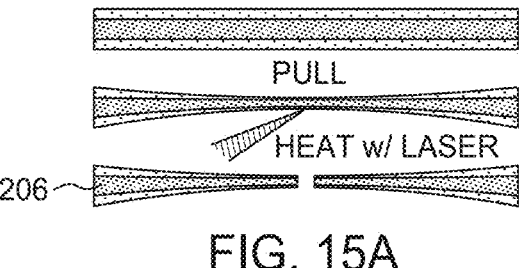
FIG. 15A illustrates a schematic of pipets prepared via pulling of capillaries and filled with electrolyte according to an embodiment of the disclosure.
Figure 15B:
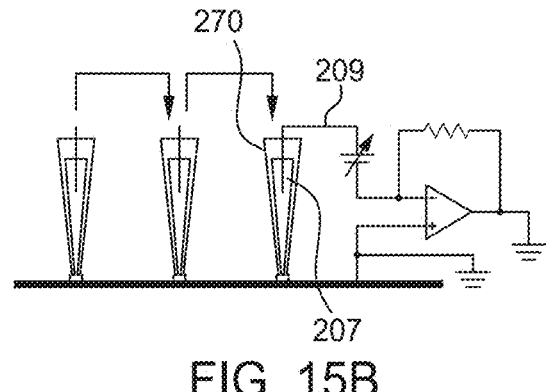
FIG. 15B illustrates a schematic of the pipets being moved from contact point to contact point to form nanoparticles according to an embodiment of the disclosure.
Figure 15C:
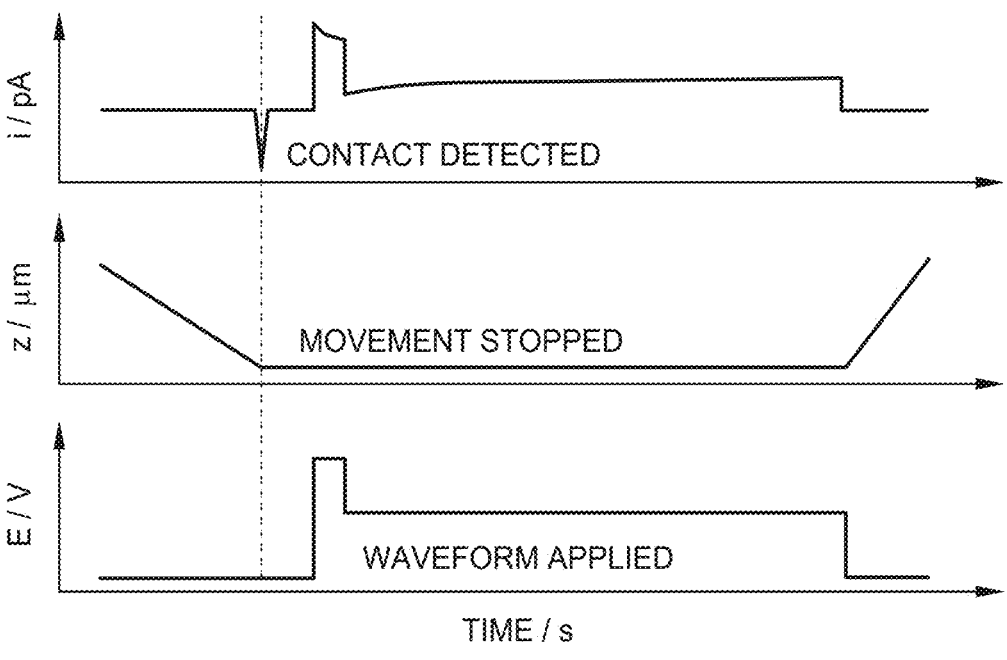
FIG. 15C illustrates data that a pipet contact is recognized by a spike in recorded current, movement is stopped, and potential waveform being applied according to an embodiment of the disclosure.

In one embodiment, Au nanoparticle arrays are fabricated with SECCM, a pipet-based microscopy technique illustrated in FIG. 15. Referring to FIG. 15A, the method includes fabricating the SECCM pipets 206 from quartz capillary tubes (1 mm OD, 0.5 mm ID) via laser-assisted pipet pulling. Small (typically <1 µm terminal diameter) pipets are filled with the electrolyte solution HAuCl$_4$, and a gold wire 209 is inserted. Referring to FIG. 15B, the method includes the SECCM pipet contacting an array of contact points 210 across a substrate 208, creating a miniaturized electrochemical cell at each contact point. Referring to FIG. 15C, the method includes the first and second piezo 112a, 122b detecting the contact between the pipet 206 and the substrate 208. The method also includes halting the movement of the pipet 206 toward the substrate 208 for a period of time as a waveform potential is applied between the substrate 208 and the wire 209. This potential results in the formation of the nanoparticle 202 as seen in FIGS. 13-14.

In another embodiment, the method further comprises functionalizing the nanoparticles 202 in the nanoparticle array 201 with analyte responsive polymers 270. The nanoparticle 202 can be functionalized with analyte responsive polymers 270, which further includes a recognition element

272 that is capable of multiplexed sensing. Pipet-based probes, similar to those employed in for electrodeposition, are used to locally address individual nanoparticles 202, enabling multianalyte detection within nanoparticle arrays 201. In order to accomplish this, the method further comprises conjugating a terminus 274 of the analyte responsive polymer 270 to the nanoparticle 202, where the terminus is distal to the recognition element 272. The pipet based probe is lowered onto the substrate 208 until a small current spike is detected. The probe is then held in contact for a set period of time, and then retracts and moves to the nanoparticle 202 at the next contact point 210. The analyte responsive polymer 270 remains on the substrate 208 due to the wetting of the nanoparticle array 201 on the substrate, and the analyte responsive polymers react with the nanoparticles 202 surface for a specific period.

Referring to FIG. 14, the functionalization of the Au nanoparticles 202 with ELPs is shown. The pipet-based probe can be filled with an aqueous solution containing the ELPs and an appropriate buffer which doubles as an electrolyte (e.g, 10 mM Tris with 5 mM TCEP at ph=8). Microscale pipets are used for chemically addressing surfaces. The method of functionalizing the AU nanoparticles 202 begins with depositing the Au nanoparticles onto conducting substrates 208 through electrodeposition within the meniscus of the electrolyte-filled pipet, as described above. Next, the method includes locally delivering the ELPs to the AU nanoparticles. Similar pipets are used for the local delivery of ELP transduction enhancement elements, utilizing the robust surface chemistry of Au to anchor species to these well-defined surfaces. Concentration, environment (i.e., humidity and temperature down to 4° C.), solvent conditions, and probe diameters (~¼ of the lateral spacing for any given array, ensuring individual nanoparticle 202 can be addressed) are selected such that the ELP is present as soluble monomers (i.e., below the transition temperature; $T_t$).

The method includes the ELPs attaching to the surface of the Au nanoparticles using Au-thiol bonds. Varying the process parameters, such as multiple, orthogonal, or site-specific bioconjunction strategies, can yield optimal ELP function. Conjugation occurs at the terminus in order to enforce a "binding-end-out" orientation of the analyte responsive polymer relative to the surface of the nanoparticle 202. The ELP functionalization of the modified Au nanoparticle 202 can be evaluated through electrochemically-active surface area (EASA) measurement schemes for Au which rely on copper (Cu) potential deposition or Au oxide film formation. By using EASA, the fraction of the Au nanoparticle surfaces covered by ELP fusion proteins can be determined. By using the methods described to fabricate the nanoparticle arrays based on SECCM techniques, a 75×75 member array of functionalized 50-100 nm nanoparticles 202 can be fabricated in 1 hour, and the total active sensor dimensions are 1.2 mm×1.2 mm. Once optimized, the uniformity of nanoparticle electrodeposition is greater than 95% and variation in ELP surface coverage is smaller than 10%.

The method further includes reacting an analyte 276 to the recognition element 272 and producing an electrochemical signal based on the reaction. Finally, the method includes measuring the electrochemical signal using the nanoparticles 202 as an electrode to a measurement device in order to monitor surface events of the analyte responsive polymer 270.

Referring to FIG. 14, a planar ITO substrate 208 can first be patterned via standard photolithography methods into several independent electrodes. Au nanoparticle 202 are then deposited onto these electrodes and functionalized as described above, and an insulating film is applied to cover non-functionalized areas of the sensor.

Functionalization of the Au nanoparticle arrays rely on heterogeneous chemical reactions and slow reaction kinetics could limit the efficacy of the described functionalization approach. Furthermore, the described microdroplet functionalization approach, due to evaporation of the solvent medium, could exacerbate the slow reaction kinetics. In one embodiment, the humidity of the environmental chamber can be adjusted (e.g. $H_2O$ saturation) to enable longer reaction times. In another embodiment, the probe is held in position for a longer period of time to increase reaction times.

Figures 16A, 16B, 16C:
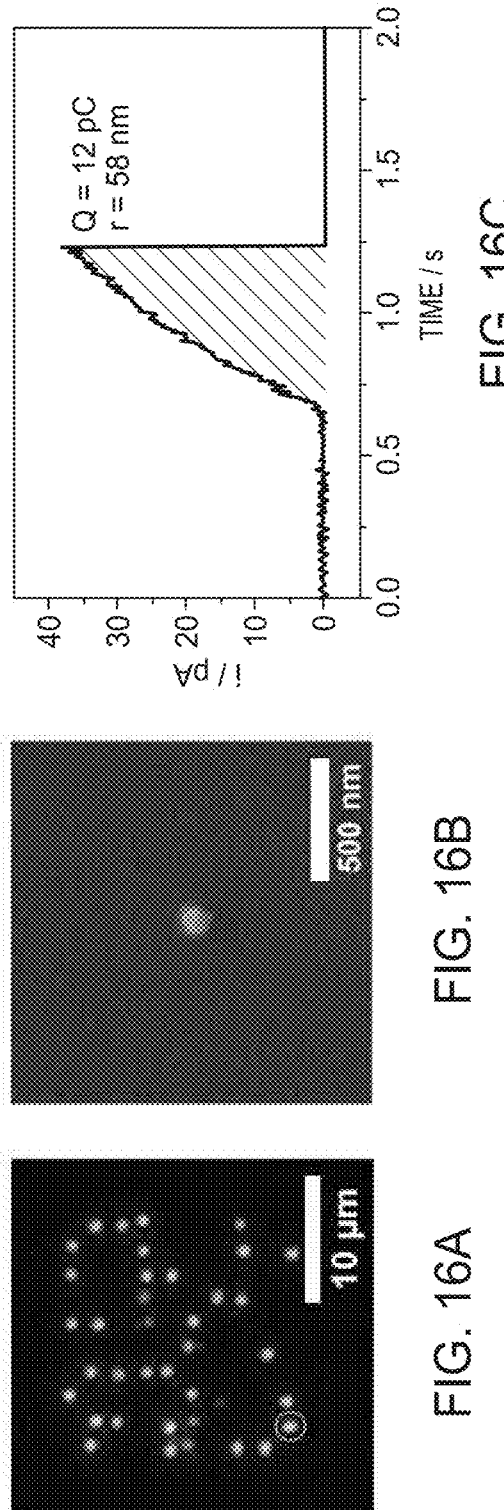
FIG. 16A illustrates a dark field optical image of an electrodeposited Au particle array on indium tin oxide according to an embodiment of the disclosure.
FIG. 16B illustrates a scanning electron micrograph of the individual Au particle illustrated in FIG. 16A.
FIG. 16c illustrates amperometric trace data recorded during the deposition of the particle of FIGS. 16A and 16B.

Array fabrication according to the embodiments described herein has been utilized to demonstrate the utilization of electrodeposition to form arrays of hemispherical Au particles, as illustrated in FIGS. 16A-C. FIG. 16A shows favorable optical properties of Au nanoparticles which enable direct visualization via dark field microscopy. FIG. 16B confirms via scanning electron microscopy that the deposited particles possess an average radius of approximately 60 nm, consistent with the 12 pC of charge passed in the fabrication of the arrays. FIG. 16C shows amperometric trace data recorded during the deposition of the particle of FIGS. 16a and 16b.

The fabricated arrays can be characterized via optical microscopy and scanning electron microscopy (SEM) imaging. Optical microscopy can provide quick visual confirmation of particle formation and μm-scale spatial distributions. SEM imaging can be employed to obtain more detailed information about the size and shape of the fabricated particles.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed here.

Furthermore, although embodiments disclosed herein may achieve advantages over other possible solutions or over the prior art, whether or not a particular advantage is achieved by a given embodiment is not limiting of the scope of the present disclosure. Thus, the aspects, features, embodiments, and advantages described are merely illustrative and are not considered elements or limitations of the appended claims except where explicitly recited in a claim(s). Likewise, reference to "the disclosure" shall not be construed as a generalization of any inventive subject matter disclosed herein and shall not be considered to be an element or limitation of the appended claims except where explicitly recited in a claim(s).

While the foregoing is directed to embodiments of the present disclosure, other and further embodiments of the disclosure may be devised without departing from the basic scope thereof, and the scope thereof is determined by the claims that follow.

What is claimed is:

1. A method of fabricating an array of nanoparticles, the method comprising:

forming a solution containing a material precursor and an electrolyte;

loading the solution into a pipet;

inserting a wire into the solution;

bringing the pipet into contact with a substrate;

applying an electrical bias between the substrate and the wire;

forming a nanoparticle via electrodeposition;

controlling a size of the nanoparticle using a two-step potential waveform;

repeating the steps of bringing the pipet into contact with the substrate, applying an electrical bias between the substrate and the wire, and forming a nanoparticle via electrodeposition across an array of contact points to create the array of nanoparticles; and rinsing the substrate with a solvent to remove residual electrolytes.

2. The method of claim 1, the method further comprising terminating the potential once a desired amount of charge has passed.

3. The method of claim 2, wherein the solution further includes an analyte responsive polymer, the method further comprising functionalizing the nanoparticles in the nanoparticle array with analyte responsive polymers.

4. The method of claim 3, wherein the analyte responsive polymers include a recognition element, wherein the recognition element is capable of multiplexed sensing.

5. The method of claim 4, the method further comprising conjugating a terminus of the analyte responsive polymer to the nanoparticle, the terminus being distal to the recognition element.

6. The method of claim 5, the method further comprising reacting an analyte to the recognition element, producing an electrochemical signal based on a reaction, and measuring the electrochemical signal using the nanoparticles to monitor surface events of the analyte responsive polymer.

7. A method of fabricating an array of nanoparticles, the method comprising:

fabricating a scanning electrochemical cell microscopy (SECCM) pipet;

forming a solution comprising a material precursor and an electrolyte;

loading the solution into the SECCM pipet;

inserting a wire into the solution;

bringing the SECCM pipet into contact with a substrate;

applying an electrical bias between the substrate and the wire;

forming a nanoparticle via electrodeposition;

controlling a size of the nanoparticle using a potential waveform;

repeating the bringing the pipet into contact with the substrate, applying an electrical bias between the substrate and the wire, and forming a nanoparticle via electrodeposition across an array of contact points to create the array of nanoparticles; and rinsing the substrate with a solvent to remove residual electrolytes.

8. The method of claim 7, wherein fabricating the SECCM pipet comprises fabricating the SECCM pipet from quartz capillary tubes via laser assisted pipet pulling.

9. The method of claim 7, further comprising detecting the contact between the SECCM pipet and the substrate via a first piezo and a second piezo.

10. The method of claim 7, further comprising halting a movement of the SECCM pipet toward the substrate for a period of time as the two-step potential waveform is applied between the substrate and the wire.

11. The method of claim 7, further comprising creating an electrochemical cell at each contact point where the SECCM pipet is in contact with the substrate.

12. The method of claim 7, wherein the wire is a gold wire and the solution is a $HAuCl_4$ solution.

13. The method of claim 7, wherein the SECCM pipet has a diameter of less than 1 μm.

14. A method of fabricating an array of nanoparticles, the method comprising:

forming a solution comprising a material precursor, and an electrolyte;

loading the solution into a pipet;

inserting a wire into the solution;

bringing the pipet into contact with a substrate;

applying an electrical bias between the substrate and the wire;

forming a nanoparticle via electrodeposition;

locally delivering an elastin-like polymer (ELP) to the nanoparticle;

repeating the bringing the pipet into contact with the substrate, applying an electrical bias between the substrate and the wire, and forming a nanoparticle via electrodeposition across an array of contact points to create the array of nanoparticles;

rinsing the substrate with a solvent to remove residual electrolytes; and functionalizing the nanoparticles in the array of nanoparticles with the ELP.

15. The method of claim 14, wherein the nanoparticles are gold nanoparticles.

16. The method of claim 14, further comprising locally delivering the ELP to the nanoparticle.

17. The method of claim 16, wherein locally delivering the ELP to the nanoparticle further comprises using a scanning electrochemical cell microscopy (SECCM) pipet.

18. The method of claim 17, wherein the SECCM pipet has a diameter of less than 1 μm.

19. The method of claim 14, further comprising attaching the ELP to a surface of the nanoparticle.

20. The method of claim 14, wherein the ELP is a soluble monomer.

21. A method of fabricating an array of nanoparticles, the method comprising:

forming a solution containing a material precursor and an electrolyte;

loading the solution into a pipet;

inserting a wire into the solution;

bringing the pipet into contact with a substrate;

applying an electrical bias between the substrate and the wire;

forming a nanoparticle via electrodeposition;

controlling a size of the nanoparticle by terminating the electrical bias once a desired amount of charge has passed;

repeating the steps of bringing the pipet into contact with the substrate, applying an electrical bias between the substrate and the wire, and forming a nanoparticle via electrodeposition across an array of contact points to create the array of nanoparticles; and rinsing the substrate with a solvent to remove residual electrolytes.

22. The method of claim 21, wherein the solution further includes an analyte responsive polymer, the method further comprising functionalizing the nanoparticles in the nanoparticle array with analyte responsive polymers.

23. The method of claim 22, wherein the analyte responsive polymers include a recognition element, wherein the recognition element is capable of multiplexed sensing.

24. The method of claim 23, the method further comprising conjugating a terminus of the analyte responsive polymer to the nanoparticle, the terminus being distal to the recognition element.

25. The method of claim 24, the method further comprising reacting an analyte to the recognition element, producing an electrochemical signal based on a reaction, and measuring the electrochemical signal using the nanoparticles to monitor surface events of the analyte responsive polymer.

\* \* \* \* \*